(12) United States Patent
Routh et al.

(10) Patent No.: US 7,647,102 B2
(45) Date of Patent: *Jan. 12, 2010

(54) CARDIAC CONTRACTILITY MODULATION DEVICE HAVING ANTI-ARRHYTHMIC CAPABILITIES AND METHOD OF OPERATING THEREOF

(75) Inventors: Andre G. Routh, Lake Jackson, TX (US); Edward Haluska, Angleton, TX (US); Nissim Darvish, Haifa (IL); David Prutchi, Lake Jackson, TX (US); Ziv Belsky, Haifa (IL)

(73) Assignee: Impulse Dynamics N.V., Curacao (AN)

( * ) Notice: Subject to any disclaimer, the term of this patent is extended or adjusted under 35 U.S.C. 154(b) by 226 days.

This patent is subject to a terminal disclaimer.

(21) Appl. No.: 11/283,401

(22) Filed: Nov. 18, 2005

(65) Prior Publication Data

US 2006/0212079 A1    Sep. 21, 2006

Related U.S. Application Data

(63) Continuation of application No. 10/111,515, filed on Oct. 30, 2002, now Pat. No. 6,993,385.

(51) Int. Cl.
*A61N 1/00*    (2006.01)
(52) U.S. Cl. .......................................................... 607/5
(58) Field of Classification Search ................. 607/4–28
See application file for complete search history.

(56) References Cited

U.S. PATENT DOCUMENTS 3,572,345 A    3/1971  Auphan
3,587,567 A    6/1971  Schiff (Continued)

FOREIGN PATENT DOCUMENTS

EP    0148687    7/1985

(Continued)

OTHER PUBLICATIONS

Zipes et al. "Cardiac Electrophysiology—From Cell to Bedside", Saunders Co., 4th Ed., 1990.

(Continued)

*Primary Examiner*—Scott M Getzow
(74) *Attorney, Agent, or Firm*—William H. Dippert; Eckert Seamans Cherin & Mellott, LLC

(57) ABSTRACT

A cardiac contractility modulating (CCM) device (30) includes an anti-arrhythmic therapy unit (38) for detecting a cardiac arrhythmia in a heart (2) of a patient based on processing electrical signals related to cardiac activity sensed at the heart, and for delivering anti-arrhythmic therapy to the heart. The device includes a cardiac contractility modulating (CCM) unit (40) capable of delivering cardiac contractility modulating (CCM) signals to the heart for modulating the contractility of a portion of the heart. The device may provide to the anti-arrhythmic therapy unit control signals associated with the delivery of the CCM signals to the heart. The control signals may be used to prevent interference of the CCM signals with the detecting of the cardiac arrhythmia. The device (30) includes a power source. The device may be an implantable device or a non-implantable device. The device may also include a pacing unit.

18 Claims, 4 Drawing Sheets

U.S. PATENT DOCUMENTS

| | | |
|---|---|---|
| 3,651,805 A | 3/1972 | Breiling |
| 3,942,536 A | 3/1976 | Mirowski et al. |
| 3,952,750 A | 4/1976 | Mirowski et al. |
| 4,030,509 A | 6/1977 | Heilman et al. |
| 4,106,494 A | 8/1978 | McEachern |
| 4,164,216 A | 8/1979 | Person |
| 4,184,493 A | 1/1980 | Langer et al. |
| 4,202,340 A | 5/1980 | Langer et al. |
| 4,223,678 A | 9/1980 | Langer et al. |
| 4,237,895 A | 12/1980 | Johnson |
| 4,273,114 A | 6/1981 | Barkalow et al. |
| 4,312,354 A | 1/1982 | Walters |
| 4,316,472 A | 2/1982 | Mirowski et al. |
| 4,384,585 A | 5/1983 | Zipes |
| 4,387,717 A | 6/1983 | Brownlee et al. |
| 4,403,614 A | 9/1983 | Engle et al. |
| 4,407,288 A | 10/1983 | Langer et al. |
| 4,440,172 A | 4/1984 | Langer |
| 4,506,680 A | 3/1985 | Stokes |
| 4,543,738 A | 10/1985 | Mower |
| 4,543,956 A | 10/1985 | Herscovici |
| 4,554,922 A | 11/1985 | Prystowsky et al. |
| 4,559,946 A | 12/1985 | Mower |
| 4,559,947 A | 12/1985 | Renger et al. |
| 4,566,456 A | 1/1986 | Koning et al. |
| 4,572,191 A | 2/1986 | Mirowski et al. |
| 4,628,934 A | 12/1986 | Pohndorf et al. |
| 4,651,716 A | 3/1987 | Forester et al. |
| 4,674,508 A | 6/1987 | Decote |
| 4,679,572 A | 7/1987 | Baker |
| 4,690,155 A | 9/1987 | Hess |
| 4,726,279 A | 2/1988 | Kepler et al. |
| 4,726,379 A | 2/1988 | Altman et al. |
| 4,765,341 A | 8/1988 | Mower et al. |
| 4,830,006 A | 5/1989 | Haluska et al. |
| 4,928,688 A | 5/1990 | Mower |
| 4,971,058 A | 11/1990 | Pless et al. |
| 4,979,507 A | 12/1990 | Heinz et al. |
| 4,998,531 A | 3/1991 | Bocchi et al. |
| 5,003,976 A | 4/1991 | Alt |
| 5,020,544 A | 6/1991 | Dahl et al. |
| 5,022,396 A | 6/1991 | Watanabe |
| 5,044,375 A | 9/1991 | Bach, Jr. et al. |
| 5,083,564 A | 1/1992 | Scherlag |
| 5,087,243 A | 2/1992 | Avitall |
| 5,097,832 A | 3/1992 | Buchanan |
| 5,111,815 A | 5/1992 | Mower |
| 5,129,394 A | 7/1992 | Mehra |
| 5,137,021 A | 8/1992 | Wayne et al. |
| 5,154,501 A | 10/1992 | Svenson et al. |
| 5,156,147 A | 10/1992 | Warren et al. |
| 5,156,149 A | 10/1992 | Hudrlik |
| 5,161,527 A | 11/1992 | Nappholz et al. |
| 5,163,428 A | 11/1992 | Pless |
| 5,172,699 A | 12/1992 | Svenson et al. |
| 5,184,620 A | 2/1993 | Cudahy et al. |
| 5,199,428 A | 4/1993 | Obel et al. |
| 5,205,284 A | 4/1993 | Freeman |
| 5,213,098 A | 5/1993 | Bennett et al. |
| 5,236,413 A | 8/1993 | Feiring |
| 5,281,219 A | 1/1994 | Kallok |
| 5,282,785 A | 2/1994 | Shapland et al. |
| 5,284,491 A | 2/1994 | Sutton et al. |
| 5,286,254 A | 2/1994 | Shapland et al. |
| 5,305,745 A | 4/1994 | Zacouto |
| 5,320,642 A | 6/1994 | Scherlag |
| 5,320,643 A | 6/1994 | Roline et al. |
| 5,346,506 A | 9/1994 | Mower et al. |
| 5,353,800 A | 10/1994 | Pohndorf et al. |
| 5,366,486 A | 11/1994 | Zipes et al. |
| 5,368,040 A | 11/1994 | Carney |
| 5,370,665 A | 12/1994 | Hudrlik |
| 5,386,837 A | 2/1995 | Sterzer |
| 5,387,419 A | 2/1995 | Levy et al. |
| 5,391,192 A | 2/1995 | Lu et al. |
| 5,391,199 A | 2/1995 | Ben Haim |
| 5,398,683 A | 3/1995 | Edwards et al. |
| 5,415,629 A | 5/1995 | Henley |
| 5,417,717 A | 5/1995 | Salo et al. |
| 5,419,763 A | 5/1995 | Hildebrand |
| 5,425,363 A | 6/1995 | Wang |
| 5,443,485 A | 8/1995 | Housworth et al. |
| 5,443,489 A | 8/1995 | Ben-Haim |
| 5,447,520 A | 9/1995 | Spano et al. |
| 5,458,568 A | 10/1995 | Racchini et al. |
| 5,464,020 A | 11/1995 | Lerner |
| 5,468,254 A | 11/1995 | Hahn et al. |
| 5,472,453 A | 12/1995 | Alt |
| 5,476,484 A | 12/1995 | Hedberg |
| 5,476,485 A | 12/1995 | Weinberg et al. |
| 5,476,497 A | 12/1995 | Mower et al. |
| 5,482,052 A | 1/1996 | Lerner |
| 5,499,971 A | 3/1996 | Shapland et al. |
| 5,501,662 A | 3/1996 | Hofmann |
| 5,514,162 A | 5/1996 | Bomzin et al. |
| 5,520,642 A | 5/1996 | Bigagli et al. |
| 5,531,764 A | 7/1996 | Adams et al. |
| 5,540,722 A | 7/1996 | Clare et al. |
| 5,549,646 A | 8/1996 | Katz et al. |
| 5,556,421 A | 9/1996 | Prutchi et al. |
| 5,568,809 A | 10/1996 | Ben-Haim |
| 5,571,143 A | 11/1996 | Hoegnelld et al. |
| 5,584,803 A | 12/1996 | Stevens et al. |
| 5,584,868 A | 12/1996 | Salo et al. |
| 5,587,200 A | 12/1996 | Lorenz et al. |
| 5,601,609 A | 2/1997 | Duncan |
| 5,601,611 A | 2/1997 | Fayram et al. |
| 5,601,615 A | 2/1997 | Markowitz et al. |
| 5,622,687 A | 4/1997 | Krishnan et al. |
| 5,626,622 A | 5/1997 | Cooper |
| 5,634,899 A | 6/1997 | Shapland et al. |
| 5,649,966 A | 7/1997 | Noren et al. |
| 5,651,378 A | 7/1997 | Matheny et al. |
| 5,662,687 A | 9/1997 | Hedberg et al. |
| 5,674,251 A | 10/1997 | Combs et al. |
| 5,674,259 A | 10/1997 | Gray |
| 5,683,431 A | 11/1997 | Wang |
| 5,687,734 A | 11/1997 | Dempsey et al. |
| 5,713,935 A | 2/1998 | Prutchi et al. |
| 5,720,768 A | 2/1998 | Verboven-Nelissen |
| 5,735,876 A | 4/1998 | Kroll et al. |
| 5,738,096 A | 4/1998 | Ben Haim |
| 5,738,105 A | 4/1998 | Kroll |
| 5,749,906 A | 5/1998 | Kieval et al. |
| 5,755,740 A | 5/1998 | Nappholtz |
| 5,782,876 A | 7/1998 | Flammang |
| 5,782,881 A | 7/1998 | Lu et al. |
| 5,792,198 A | 8/1998 | Nappholz |
| 5,792,208 A | 8/1998 | Gray |
| 5,797,967 A | 8/1998 | Kenknight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,861,012 A | 1/1999 | Stroebel |
| 5,865,787 A | 2/1999 | Shapland et al. |
| 5,871,506 A | 2/1999 | Mower |
| 5,906,607 A | 5/1999 | Taylor et al. |
| 5,913,876 A | 6/1999 | Taylor et al. |
| 5,927,284 A | 7/1999 | Borst et al. |
| 5,928,270 A | 7/1999 | Ramsey, III |
| 6,032,074 A | 2/2000 | Collins |
| 6,032,672 A | 3/2000 | Taylor |
| 6,041,252 A | 3/2000 | Walker et al. |

| | | | |
|---|---|---|---|
| 6,067,470 A | 5/2000 | Mower | |
| 6,071,305 A | 6/2000 | Brown et al. | |
| 6,086,582 A | 7/2000 | Altman et al. | |
| 6,136,019 A | 10/2000 | Mower | |
| 6,141,586 A | 10/2000 | Mower | |
| 6,144,880 A | 11/2000 | Ding et al. | |
| 6,151,586 A | 11/2000 | Brown | |
| 6,152,882 A | 11/2000 | Prutchi | |
| 6,178,351 B1 | 1/2001 | Mower | |
| 6,223,072 B1 | 4/2001 | Mika et al. | |
| 6,233,484 B1 | 5/2001 | Ben-Haim et al. | |
| 6,233,487 B1 | 5/2001 | Mika et al. | |
| 6,240,314 B1 | 5/2001 | Plicchi et al. | |
| 6,263,242 B1 | 7/2001 | Mika et al. | |
| 6,263,460 B1 | 7/2001 | Spilo et al. | |
| 6,292,693 B1 | 9/2001 | Darvish et al. | |
| 6,295,470 B1 | 9/2001 | Mower | |
| 6,317,631 B1 | 11/2001 | Ben-Haim et al. | |
| 6,337,995 B1 | 1/2002 | Mower | |
| 6,341,235 B1 | 1/2002 | Mower | |
| 6,343,232 B1 | 1/2002 | Mower | |
| 6,360,123 B1 | 3/2002 | Kimchi et al. | |
| 6,360,126 B1 | 3/2002 | Mika et al. | |
| 6,370,430 B1 | 4/2002 | Mika et al. | |
| 6,411,847 B1 | 6/2002 | Mower | |
| 6,424,866 B2 | 7/2002 | Mika et al. | |
| 6,459,928 B2 | 10/2002 | Mika et al. | |
| RE38,119 E | 5/2003 | Mower | |
| 6,993,385 B1 | 1/2006 | Routh et al. | |
| 7,027,863 B1 | 4/2006 | Prutchi et al. | |
| 2001/0031994 A1 | 10/2001 | Mika et al. | |

FOREIGN PATENT DOCUMENTS

| | | |
|---|---|---|
| EP | 0314078 | 5/1989 |
| EP | 1284786 | 2/2003 |
| JP | S62-275471 | 11/1987 |
| JP | 04-117967 | 4/1992 |
| JP | 04-365493 | 12/1992 |
| JP | 07-126600 | 5/1995 |
| JP | 08-243176 | 9/1996 |
| WO | WO 92/00716 | 1/1992 |
| WO | WO 95/08316 | 3/1995 |
| WO | WO 97/25098 | 7/1997 |
| WO | WO 97/25101 | 7/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 00/04947 | 2/2000 |
| WO | WO 00/57952 | 10/2000 |
| WO | WO 01/30139 | 5/2001 |
| WO | WO 01/30436 | 5/2001 |
| WO | WO 01/87134 | 11/2001 |

OTHER PUBLICATIONS

Antman et al. "Treatment of 150 Cases of Life-Threatening Digitalis Intoxication With Digoxin-Specific Fab Antibody Fragments", Circulation, 81(6): 1744-1752, 1990.

Antoni et al. "Polarization Effects of Sinusoidal 50-Cycle Alternating Current on Membrane Potential of Mammalian Cardiac Fibres", Pflügers Archiv European Journal of Physiology, 314(4): 274-291, 1970. Abstract.

Bargheer et al. "Prolongation of Monophasic Action Potential Duration and the Refractory Period in the Human Heart by Tedisamil, A New Potassium-Blocking Agent", Journal European Heart, 15(10): 1409-1414, 1994.

Bers "Excitation Contraction Coupling and Cardiac Contractile Force", Internal Medicine, 237(2): 17, 1991.

Borst et al. "Coronary Artery Bypass Gratting Without Cardiopulomonary Bypass and Without Interuption of Native Coronary Flow Using A Novel Anastomosis Site Restraining Device (Octupus)", Journal of the American College of Cardiology, 27(6): 1356-1364, 1996.

Cano et al. "Dose-Dependent Reversal of Dixogin-Inhibited Activity of An In-Vitro Na+K+ATPase Model by Digoxin-Specific Antibody", Toxicology Letters, 85(2): 107-1011, 1996.

Cazeau et al. "Multisite Pacing for End-Stage Heart Failure: Early Experience", Pacing and Clinical Electrophysiology, 19(11): 1748-1757, 1996.

Cooper "Postextrasystolic Potention. Do We Really Know What It Means and How to Use It?", Circulation, 88: 2962-2971, 1993.

Dillon "Optical Recordings in the Rabbit Heart Show That Defibrillation Strength Shocks Prolong the Duration of Depolarization and the Refractory Period", Circulation Research, 69: 842-856, 1991.

Dillon "Synchronized Repolarization After Defibrillation Shocks. A Possible Component of the Defibrillation Process Demonstration by Optical Recordings in Rabbit Heart", Circulation, 85(5): 1865-1878, 1992.

Fain et al. "Improved Internal Defibrillation Efficacy With A Biphasic Waveform", American Heart Journal, 117(2): 358-364, 1989.

Fleg et al. "Impact of Age on the Cardiovasvular Response to Dynamic Upright Exercise in Healthy Men and Women", Journal of Applied Physiologyl, 78: 890-900, 1995.

Foster et al. "Acute Hemodynamic Effects of Atrio—Biventricular Padng in Humans", The Society of Thoracic Surgeons, 59: 294-300, 1995.

Franz "Bridging the Gap Between Basic Clinical Electrophysiology: What Can Be Learned From Monophasic Action Potential Recordings?", Journal Cardiovasc Electrophysiology, 5(8): 699-710, 1994, Abstract.

Franz "Method and Theory of Monophasic Action Potential Recording", Prog. Cardiovasc Dis, 33(6): 347-368, 1991.

Fromer et al. Ultrarapld Subthreshold Stimulation for Termination of Atriventricular Node Reentrant Tachycardia, Journal of the American College Cardiology, 20: 879-883, 1992.

Fu et al. "System Identification of Electrically Coupled Smooth Music Cells: The Passive Electrically Coupled Smooth Muscle Cells: The Passive Electrical Properties", IEEE Transactions on Biomedical Engineering, 38(11): 1130-1140, 1991.

Gill et al. "Refractory Period Extension During Ventricular pacing at Fibrillatory pacing Rates", pacing Clin. Elctrophysiol, 20(3): 647-653, 1997.

Ham et al. "Classification of Cardiac Arrhythmias Using Fuzzy Artmap", IEEE Transactions on Biomedical Engineering, 43(4): 425-429, 1996, Abstract.

Hoffman et al. "Effects of Postextrasystolic Potentiation on Normal and Failing Hearts", Bulletin of the New York Academy of Medicine, 41(5): 498-534, 1965.

Josephson "Clinical Cardiac Electrophysiology: Techniques and Interpertations", Lea & Febiger, 2nd Ed., 2 P., 1991.

Knisley et al. "Prolgongation and Shortening of Action Potentials by Electrical Shocks in Frog Ventricular Muscle", American Journal of Physiology, 266(6): H2348-H2358, 1994.

Koller et al. "Relation Between Repolarization and Refractoriness During Programmed Electrical Stimulation in the Human Right Ventricle", Circulation, 91: 2378-2384, 1995.

Langberg et al. "Identification of Ventricular Tachycardia With Use of the Morphology of the Endocardial Electrogram", Circulation, 77: 1363-1369, 1988.

Matheny et al. "Vagus Nerve Stimulation as A Method to Temporarily Slow or Arrest the Heart", Annals of Thoracic Surgery, 63(6): S28-29, 1997.

McVeigh et al. "Noninvasive Measurement of Transmural Gradients in Myocardial Strain With MR Imaging", Radiology, 180(3): 677-684, 1991.

Moran et al. "Digoxin-Specific Fab Fragments Impair Renal Function in the Rat", Journal of Pharmacy and Pharmacology, 46(10): 854-856, 1994.

Paul et al. "Automatic Recognition of Ventricular Arrhythmias Using Temporal Electrogram Analysis", PACE, 14: 1265-1273, 1991.

Xue et al. "Neural-Network-Based Adaptive Matched Filtering for QRS Detection", IEEE Transactions on Biomedical Engineering, 39(4): 317-329, 1992, Abstract.

Shumaik et al. "Oleander Poisoning: Treatment With Digoxin-Specific Fab Antibody Fragments", Annals of Emergency Medicine, 17(7): 732-735, 1988.

Sweeny et al. "Countershock Strength-Duration Relatlonship for Myocardial Refractory period Extension", Academic Emergency medicine, 2(1): 57-62, 1995.

Sweeny et al. "Refractory Interval After Transcardiac Shocks During Ventricular Fibrillation", Circulation, 94(11): 2947-2952, 1996.

Sweeny et al. "Ventricular Refractory Period Extension Caused by Defibrillation Shocks", Circulation, 82(3): 965-972, 1990.

Talit et al. "The Effect of External Cardiac Pacing on Stroke Volume", pace, 13(5): 598-602, 1990.

Thakor et al. "Effect of Varying Pacing Waveform Shapes on Propagation and Hemodynamics in the Rabbit Heart", The American Journal of Cardiology, 79(6A): 36-43, 1997.

Tsong "Electroporation of Cell Membranes", Biophysical Journal, 60: 297-306, 1991.

Verrier et al. "Electrophysiologic Basis for T Wave Alternans as An Index of Vulnerability to Ventricular Fibrillation", Journal of Cardiovascular Electrophysiology, 5(5): 445-461, 1994. Abstract.

Webster Design of Cardiac Pacemakers, IEEE Press, p. xi-xiii, 1995.

Wessale et al. "Stroke Volume and the Three Phase Cardiac Output Rate Relationship With Ventricular Pacing", PACE, 13: 673-680, 1990.

Wirtzfeld et al. "Physiological Pacing: Present Status and Future Developments", Pace, 10(Part I): 41-57, 1987. Abstract.

Berne et al. "Electrical Activity of the Heart", Cardiovascular Physiology, 7th Ed.(Chap.2): 7-8, 1997.

Day "Tetralogy of Fallot. Introduction", http://picuBOOK.net/1998/11-02(el).html.

Pappone et al. "Cardiac Contractility Modulation by Electric Currents Applied During the Refractory Period in Patients With Heart Failure Secondary to Ischemic or Idiopathic Dilated Cardiomyopathy", The American Journal of Cardiology, 90: 1307-1313, 2002.

Van Hare "The Latest Tetralogy of Fallot Discussion With Graphical Support Including Video of Echocardiography and Catheterization", PicuBook, On-Line Resource for Pediatric Critical Care, 4 P., 2004. http://pedsccm.wustl.edu/All-Net/english/cardpage/ electric/CVsurg/dysrh-3a.htm.

Berne et al. "Electrical Activity of the Heart", Cardiovascular Physiology, 7th Ed.(Chap.2): 7-8, 1997.

Day "Tetralogy of Fallot. Introduction", http://picuBOOK.net/1998/11-02(el).html.

Pappone et al. "Cardiac Contractility Modulation by Electric Currents Applied During the Refractory Period in Patients With Heart Failure Secondary to Ischemic or Idiopathic Dilated Cardiomyopathy", the American Journal of Cardiology, 90: 1307-1313, 2002.

Van Hare "The Latest Tetralogy of Fallot Discussion With Graphical Support Including Video of Echocardiography and Catheterization", PicuBook, On-Line Resource for Pediatric Critical Care, 4 P., 2004. http://pedsccm.wustl.edu/All-Net/english/cardpage/ electric/CVsurg/dysrh-3a.htm.

CARDIAC CONTRACTILITY MODULATION DEVICE HAVING ANTI-ARRHYTHMIC CAPABILITIES AND METHOD OF OPERATING THEREOF

CROSS REFERENCES TO RELATED APPLICATIONS

This Patent Application is related to and claims priority from commonly owned U.S. Provisional Patent applications Ser. No. 60/161,328, filed Oct. 25, 1999 entitled "CARDIAC CONTRACTILITY MODULATION DEVICE HAVING ANTI-ARRHYTHMIC CAPABILITIES AND A METHOD OF OPERATING THEREOF", Ser. No. 60/161,899 filed Oct. 27, 1999 entitled "DEVICE FOR CARDIAC THERAPY", and Ser. No. 60/161,900 filed Oct. 27, 1999 entitled "ANTI-ARRHYTHMIC DEVICE AND A METHOD OF DELIVERING ANTI-ARRHYTHMIC CARDIAC THERAPY", all three Provisional Patent Applications are incorporated herein by reference in their entirety. Also, this patent application is a continuation of commonly owned, U.S. patent application Ser. No. 10/111,515, filed Oct. 30, 2002, now U.S. Pat. No. 6,993,385, also incorporated herein by reference in its entirety.

FIELD OF THE INVENTION

The present invention relates generally to the field of anti-arrhythmic cardiotherapy devices and more particularly to cardiac contractility modulation devices including anti-arrhythmic therapy capabilities.

BACKGROUND OF THE INVENTION

Anti-arrhythmic cardiac devices are well known in the art. Such devices include implantable and non-implantable devices which are used for detecting various types of arrhythmic conditions in a cardiac patient and for applying an appropriate anti-arrhythmic therapy to the heart.

For example, various pacemaker devices may detect various types of brady-arrhythmias (also known as bradycardias) and provide artificial pacing therapy to one or more cardiac chambers.

Other types of anti-arrhythmic devices such as cardiac defibrillators, and other anti-tachyarrhythmia devices such as defibrillator/cardioverter devices are designed to detect various different types of tachy-arrhythmias (also known as tachycardias) such as ventricular tachycardia (VT) which is a non-fibrillation type of tachy-arrhythmia and ventricular fibrillation (VF), and to provide one or more types of appropriate anti-tachycardia therapy to the heart such as anti-tachycardia pacing (ATP) therapy, cardioverting shock therapy and shock defibrillation therapy. Such devices may use multi-tiered tachy-arrhythmia detection algorithms (also known as classification algorithms) for distinguishing between VT, VF and supra-ventricular tachycardia (SVT) arising from atrial fibrillation and for applying the proper type of therapy selected from ATP therapy, low or medium energy cardioversion shock therapy, and high energy defibrillating shock therapy.

U.S. Pat. No. 4,403,614 to Engle et al. titled "IMPLANTABLE CARDIOVERTER", incorporated herein by reference, discloses an implantable cardioverter/defibrillator device capable of delivering cardioversion therapy pulses having an energy level lower than necessary for defibrillation as well as defibrillating pulses.

Some modern implantable Cardiotherapy devices are adapted to include a combination of various cardiac therapeutic modes. For example, implantable cardio-therapy devices may use a combination of anti-bradycardia pacing, ATP pacing, cardioversion and automatic defibrillating shock therapy. U.S. Pat. No. 4,830,006 to Haluska et al. titled "IMPLANTABLE CARDIAC STIMULATOR FOR DETECTION AND TREATMENT OF VENTRICULAR ARRHYTHMIAS", incorporate herein by reference, discloses a cardiac stimulator device which integrates the functions of bradycardia and anti-tachycardia pacing therapies and cardioversion and defibrillation shock therapies.

Recently, a new method of cardiotherapy has been introduced for modifying the cardiac contractility by delivering non-excitatory electrical signals to the myocardium at a selected time such that the electrical signals do not result in exciting propagating myocardial action potentials due to myocardial refractoriness. While such non-excitatory electrical signals do not lead to propagating myocardial action potentials, they may modulate the myocardial contractility in naturally or artificially paced cardiac beats.

Devices for performing this contractility modulating cardiotherapy are known as excitable tissue control (ETC) devices, and are also known as cardiac contractility modulation (CCM) devices. It is noted that the terms CCM and ETC are interchangeably used throughout the present application and refer to methods for modulating cardiac contractility by delivering non-excitatory electrical signals to the heart. Similarly, the terms CCM device and ETC device are interchangeably used throughout the present application and refer to devices adapted for modulating cardiac contractility by delivering non-excitatory electrical signals to the heart.

ETC devices modulate the activity of excitable tissues by application of non-excitatory electrical signals to the heart (or other excitable tissues) through suitable electrodes in contact with the tissue. For example, ETC devices may be used, inter alia, to increase or decrease the contractility of cardiac muscle in vitro, in vivo and in situ., as disclosed in detail in PCT application, International Publication Number WO 97/25098 to Ben-Haim et al., titled "ELECTRICAL MUSCLE CONTROLLER", incorporated herein by reference. Other methods and applications of ETC devices are disclosed in PCT applications commonly-assigned to the assignee of the present application, International Publication Number WO 98/10828, titled "APPARATUS AND METHOD FOR CONTROLLING THE CONTRACTILITY OF MUSCLES" to Ben Haim et al., incorporated herein by reference, International Publication Number WO 98/10829, titled "DRUG-DEVICE COMBINATION FOR CONTROLLING THE CONTRACTILITY OF MUSCLES" to Ben Haim et al., incorporated herein by reference and International Publication Number WO 98/10830, titled "FENCING OF CARDIAC MUSCLES" to Ben Haim et al., incorporated herein by reference, International Publications Number WO 98/10831 to Ben Haim et al., titled "CARDIAC OUTPUT CONTROLLER", incorporated herein by reference.

Further applications of the ETC including devices combining cardiac pacing and cardiac contractility modulation are disclosed in PCT Application, International Publication No. WO 98/10832, titled "CARDIAC OUTPUT ENHANCED PACEMAKER" to Ben Haim et al., co-assigned to the assignee of the present application. Such ETC devices function by applying non-excitatory electrical field signals of suitable amplitude and waveform, appropriately timed with respect to the heart's intrinsic electrical activity to selected cardiac regions. The contraction of the selected regions may be modulated to increase or decrease the stroke volume of the heart. The timing of the ETC signals must be carefully controlled since application of the ETC signal to the myocardium at an inappropriate time may be arrhythmogenic. The ETC signals must therefore be applied to the selected cardiac region within a defined time interval during which the selected cardiac region will not be stimulated by the ETC signals.

As disclosed in International Publication No. WO 98/10832, the ETC signals may be timed relative to a trigger signal which is also used as a pacing trigger, or may be timed relative to locally sensed electrogram signals.

Co-pending U.S. patent application to Mika et al., Ser. No. 09/276,460, titled "APPARATUS AND METHOD FOR TIMING THE DELIVERY OF NON-EXCITATORY ETC SIGNALS TO A HEART", filed Mar. 25, 1999, assigned to the common assignee of the present application, now U.S. Pat. No. 6,263,242, the entire specification of which is incorporated herein by reference, and the corresponding PCT application, International Application No. PCT/IL00/00126, International Publication No. WO 00/57952, disclose a method for timing the delivery of non-excitatory ETC signals to a heart using, inter alia, an alert window period for reducing the probability of delivering an improperly timed ETC signal to the heart due to spurious detection of noise or ectopic beats.

Co-pending U.S. patent application Ser. No. 09/328,068 to Mika et al., titled "APPARATUS AND METHOD FOR COLLECTING DATA USEFUL FOR DETERMINING THE PARAMETERS OF AN ALERT WINDOW FOR TIMING DELIVERY OF ETC SIGNALS TO A HEART UNDER VARYING CARDIAC CONDITIONS ", filed Jun. 8, 1999, U.S. Pat. No. 6,223,072, the entire specification of which is incorporated herein by reference, and the corresponding PCT application, International Application No. PCT/IL00/00310, disclose devices and methods for collecting patient data which is usable for the operation of a device for timing of delivery of ETC signals to the heart using, inter alia, a dynamically varying alert window period for event sensing.

Co-pending U.S. patent application Ser. No. 09/338,649 to Mika et al., titled "APPARATUS AND METHOD FOR SETTING THE PARAMETERS OF AN ALERT WINDOW USED FOR TIMING THE DELIVERY OF ETC SIGNALS TO A HEART UNDER VARYING CARDIAC CONDITIONS", filed Jun. 23, 1999, U.S. Pat. No. 6,233,487, the entire specification of which is incorporated herein by reference, and the corresponding PCT application, International Application No. PCT/IL00/00321, disclose devices and methods for timing of delivery of ETC signals to the heart using, inter alia, a dynamically varying alert window period for event sensing.

Application of ETC therapy to the heart may enhance the cardiac output without increasing the heart rate. Such therapy may be advantageously applied, inter alia, to patients having no diagnosed cardiac rhythm abnormalities as well as to patients such as congestive heart failure (CHF) patients which are particularly prone to episodes of VT or VF. Since cardiac patients such as, inter alia, CHF patients may benefit from the use of implantable or non-implantable anti-arrhythmic devices, such as defibrillators, Defibrillator/cardioverter devices and the like, it may be advantageous to implement a single device which is capable of delivering anti-arrhythmic therapy and ETC therapy to a cardiac patient. For example, such a device may be capable of delivering ETC therapy and defibrillating shock therapy to a patient, when a need for such therapy is detected.

While the various methods of timing the delivery of ETC signals to the heart disclosed in the above co-pending U.S. patent applications Ser. Nos. 09/276,460, 09/328,068 and 09/338,649 to Mika et al., and in the corresponding PCT applications, greatly reduce the probability of inducing arrhythmias due to delivery of ETC signals to the heart at a vulnerable time, it may be desirable to include anti-arrhythmia capabilities in ETC or CCM devices as a safety device in case of occurrence of tachy-arrhythmia episodes such as VT or VF, either due to a delivered ETC signal or spontaneously.

Unfortunately, the delivery of ETC signals to the myocardium may lead to electrical artifact signals sensed by the sense electrodes of the anti-arrhythmic device. Such electrical artifact signals may be erroneously detected by the event detecting circuitry of the anti-arrhythmic device as electrical events representing cardiac activation. Such spurious detection of electrical artifacts induced by ETC signals may adversely affect the detection and/or classification of cardiac tachy-arrhythmias. For example, such spurious event detection may result in classification of a normal heart rate as VT or VF leading to unnecessary and potentially dangerous defibrillating shock therapy being delivered to the heart.

Besides the increased patient risk and patient discomfort caused by such unnecessary delivery of defibrillation shock therapy, such erroneous detection of VF followed by defibrillating shock therapy may lead to unnecessary drain on the battery of the device, thus shortening the useful life in implanted devices. Additionally, in devices capable of delivering cardioversion therapy, spurious event detection caused by ETC induced electrical artifacts may result in unnecessary delivery of cardioversion therapy by the device which has the disadvantage of unnecessary battery drain and which may increase patient risk.

Another problem which may result from delivering of ETC signals to the heart of a patient which is monitored by an anti-arrhythmic device such as, inter alia, a defibrillator/cardioverter device, is the possible interference of ETC induced electrical artifacts with the operation of detection circuitry utilizing automatic gain control (AGC) or automatic threshold control (ATC). AGC methods and ATC methods are well known in the art. For example, AGC and ATC methods are disclosed by Dennis A. Brumwell et al. in Chapter 14 titled "THE AMPLIFIER: SENSING THE DEPOLARIZATION" in the book titled "IMPLANTABLE CARDIOVERTER DEFIBRILLATOR THERAPY: THE ENGINEERING-CLINICAL INTERFACE", pp. 275-302, Eds. Mark W. Kroll and Michael H. Lehmann, Kluwer Academic Publishers, USA, 1997.

ETC signal induced artifacts sensed by the defibrillator amplification circuits may cause an undesirable decrease in the gain of the amplifier circuits in defibrillators using AGC based algorithms which may lead to failure to detect VF signal. ETC signal induced artifacts sensed by the defibrillator amplification circuits may also cause an undesirable increase in the threshold level in defibrillators using ATC based algorithms which may also lead to failure to detect VF signal.

The above described interference problems may be encountered in the operation of a variety of different prior art internal cardiac defibrillator (ICD) devices and automatic internal cardioverter defibrillator (AICD) devices, including tiered therapy devices capable of delivering different types of cardiac therapy such as anti-brady-arrhythmic pacing therapy, anti-arrhythmic cardioversion therapy, anti-arrhythmic defibrillating shock therapy, variable energy shock therapy, anti-tachycardia pacing therapy (ATP) and any combination thereof in the presence of ETC signals delivered by operating CCM or ETC devices.

SUMMARY OF THE INVENTION

There is therefore provided, in accordance with a preferred embodiment of the present invention, a cardiac contractility modulating device. The device includes an anti-arrhythmic therapy unit for detecting a cardiac arrhythmia in a heart of a patient based on processing electrical signals related to cardiac activity of the heart, and for delivering anti-arrhythmic therapy to the heart in response to detecting of the cardiac arrhythmia. The device further includes a cardiac contractility modulating unit configured for delivering cardiac contractility modulating signals to the heart for modulating the contractility of at least a portion of the heart. The cardiac contractility modulating unit is operatively connected to the anti-arrhythmic unit for providing the anti-arrhythmic therapy unit with first control signals associated with the delivery of the cardiac contractility modulating signals to the heart, to prevent interference of the cardiac contractility modulating signals with the detecting of the cardiac arrhythmia by the anti-arrhythmic device. The device also includes at least one power source for energizing the anti-arrhythmic therapy unit and the cardiac contractility modulating unit.

Furthermore, in accordance with another preferred embodiment of the present invention, the anti-arrhythmic therapy unit is configured for providing the cardiac contractility modulating unit with second control signals associated with the delivery of the anti-arrhythmic therapy to the heart, to control the operation of the cardiac contractility modulating unit.

Furthermore, in accordance with another preferred embodiment of the present invention, the second control signals include control signals for disabling the delivery of cardiac contractility modulating signals to the heart by the cardiac contractility modulating unit, and control signals for enabling the delivery of cardiac contractility modulating signals to the heart by the cardiac contractility modulating unit.

Furthermore, in accordance with another preferred embodiment of the present invention, the anti-arrhythmic therapy unit is configured for delivering to the heart an anti-arrhythmic therapy selected from a defibrillating shock therapy, a cardioverting shock therapy, anti-tachycardia pacing therapy, anti-bradycardia pacing therapy, variable energy shock therapy, and any combination thereof.

Furthermore, in accordance with another preferred embodiment of the present invention, the device further includes electrodes operatively connected to the cardiac contractility modulating unit and to the anti-arrhythmic therapy unit, for sensing the electrical signals, for delivering the cardiac contractility modulating signals to the heart, and for delivering the anti-arrhythmic therapy to the heart.

Furthermore, in accordance with another preferred embodiment of the present invention, the device further includes a pacing unit for pacing at least one cardiac chamber of the heart.

Furthermore, in accordance with another preferred embodiment of the present invention, the pacing unit is connectable to one or more pacing electrodes to provide anti-bradycardia therapy to the heart.

Furthermore, in accordance with another preferred embodiment of the present invention, the device is configured for preventing or modifying the sensing of the electrical signals in response to receiving one of the first control signals.

Furthermore, in accordance with another preferred embodiment of the present invention, the device includes a sensing unit for sensing the electrical signals, the sensing unit is configured for stopping the sensing of the electrical signals within a refractory time period in response to receiving one of the first control signals.

Furthermore, in accordance with another preferred embodiment of the present invention, the device includes a detecting unit for detecting cardiac activity related events in the electrical signals. The detecting unit is configured for stopping the detecting of the cardiac activity related events within a refractory time period in response to receiving one of the first control signals.

Furthermore, in accordance with another preferred embodiment of the present invention, the refractory period is a preset refractory period.

Furthermore, in accordance with another preferred embodiment of the present invention, the duration of the refractory period is set to prevent the erroneous detection of electrical artifacts associated with the cardiac contractility modulating signals.

Furthermore, in accordance with another preferred embodiment of the present invention, the duration of the refractory period is set to prevent erroneous detection of any of the cardiac contractility modulating signal associated electrical artifacts recorded in a recording session in the patient.

Furthermore, in accordance with another preferred embodiment of the present invention, the device is configured for controllably varying the parameters of the cardiac contractility modulating signals delivered to the heart, the refractory period is a variable refractory period, and the device is configured for determining the parameters of the variable refractory period in accordance with the parameters of the cardiac contractility modulating signal delivered to the heart in each cardiac beat cycle.

Furthermore, in accordance with another preferred embodiment of the present invention, the device includes a look up table, the look up table includes data associating different parameters of the refractory period with different cardiac contractility modulating signals deliverable to the heart. The data included in the look up table is determined in a data collection session performed in the patient.

Furthermore, in accordance with another preferred embodiment of the present invention, the device includes a voltage protection unit electrically coupled to sensing electrodes disposed at or about the heart. The voltage protection unit is connected to a sensing or a detecting unit included in the device. The voltage protection unit protects the circuitry of the device from high voltages applied by the anti-arrhythmic unit to the heart. The voltage protection unit is configured for modifying the electrical signals in response to receiving one of the first control signals, prior to passing the electrical signals to the sensing unit or the detecting unit.

Furthermore, in accordance with another preferred embodiment of the present invention, the voltage protection unit includes a controllable filter unit for controllably attenuating the electrical signals in response to receiving one of the first control signals.

Furthermore, in accordance with another preferred embodiment of the present invention, the device further includes a matched filter unit configured for rejecting electrical artifact signals included in the electrical signals. The electrical artifact signals are associated with the delivery of the cardiac contractility modulating signals to the heart.

Furthermore, in accordance with another preferred embodiment of the present invention, the device further includes a processor unit in communication with the cardiac contractility modulating unit and with the anti-arrhythmic therapy unit, and a classification program operative on the processor unit to control the delivery of the anti-arrhythmic therapy to the heart in response to detection of arrhythmia types based on the classification of the determined heart rate of the heart.

Furthermore, in accordance with another preferred embodiment of the present invention, the program is adapted to correct or compensate errors in the classification of arrhythmia types.

Furthermore, in accordance with another preferred embodiment of the present invention, the errors comprise the erroneous detection of electrical artifact signals as events associated with cardiac beats. The electrical artifact signals are associated with the delivery of the of cardiac contractility modulating signals to the heart. The program is adapted to correct or compensate the errors by subtracting the number of cardiac contractility modulating signals delivered to the heart within a time period including a number of cardiac beat cycles from the number of events detected within the duration of the time period.

Furthermore, in accordance with another preferred embodiment of the present invention, the errors are due to the stopping of the sensing or of the detecting of cardiac events within a refractory time period including a portion of the cardiac beat cycle of the heart. The errors are corrected by stopping the delivery of the cardiac contractility modulating signals when the heart rate of the heart exceeds a threshold value, and performing the classification of arrhythmia types in the absence of the cardiac contractility modulating signals.

Furthermore, in accordance with another preferred embodiment of the present invention, the device is an implantable device and the cardiac contractility modulating unit, the anti-arrhythmic therapy unit and the power source are disposed within an implantable housing.

Furthermore, in accordance with another preferred embodiment of the present invention, the device further includes a telemetry unit operatively coupled to the processing unit, for telemetrically communicating with a telemetry transceiver.

Furthermore, in accordance with another preferred embodiment of the present invention, the device is disposed outside the patient and is operatively connectable to electrodes for sensing the electrical signals, for delivering the cardiac contractility modulating signals to the heart, and for delivering the anti-arrhythmic therapy to the heart.

Furthermore, in accordance with another preferred embodiment of the present invention, the device further includes at least one processing unit operatively coupled to the cardiac contractility modulating unit and to the anti-arrhythmic therapy unit, for controlling the operation of the cardiac contractility modulating unit and the anti-arrhythmic therapy unit.

Furthermore, in accordance with another preferred embodiment of the present invention, the device further includes a memory unit operatively coupled to the processing unit. The processing unit is capable of storing data in the memory unit and of retrieving data stored in the memory unit.

Furthermore, in accordance with another preferred embodiment of the present invention, the device further includes at least one timing unit operatively coupled to the processing unit, for providing timing signals to the processing unit.

Furthermore, in accordance with another preferred embodiment of the present invention, at least one of the cardiac contractility modulating unit and the anti-arrhythmic therapy unit includes a processing unit therewithin, for controlling the operation of the cardiac contractility modulating unit and the anti-arrhythmic therapy unit.

There is also provided, in accordance with a preferred embodiment of the present invention, a cardiac contractility modulating device. The device includes anti-arrhythmic therapy means for detecting a cardiac arrhythmia in a heart of a patient based on processing electrical signals related to cardiac activity of the heart and for delivering anti-arrhythmic therapy to the heart in response to detecting of the cardiac arrhythmia. The device also includes cardiac contractility modulating means configured for delivering cardiac contractility modulating signals to the heart for modulating the contractility of at least a portion of the heart. The cardiac contractility modulating means is operatively connected to the anti-arrhythmic therapy means, for providing the anti-arrhythmic therapy means with first control signals associated with the delivery of the cardiac contractility modulating signals to the heart to prevent interference of the cardiac contractility modulating signals with the detecting of the cardiac arrhythmia by the anti-arrhythmic device. The device also includes energizing means for providing power to the anti-arrhythmic therapy means and the cardiac contractility modulating means.

There is also provided, in accordance with a preferred embodiment of the present invention, a method for operating an anti-arrhythmic therapy device in a patient undergoing cardiac contractility modulation therapy by a cardiac contractility modulating device. The method includes the steps of providing an anti-arrhythmic therapy device for sensing electrical signals related to cardiac activity of the patient, for processing the electrical signals to detect a cardiac arrhythmia, and for delivering anti-arrhythmic therapy to the heart of the patient in response to the detecting of the cardiac arrhythmia. The method also includes providing a cardiac contractility modulating device for applying cardiac contractility modulating signals to the heart of the patient. The method further includes providing the anti-arrhythmic therapy device with control signals associated with the delivery of the cardiac contractility modulating signals to the heart, and modifying the sensing or the processing in response to the control signals to prevent the interference of electrical artifact signals associated with the cardiac contractility modulating signals with the detecting of cardiac arrhythmia by the anti-arrhythmic therapy device.

There is also provided, in accordance with a preferred embodiment of the present invention, a method for applying anti-arrhythmic therapy to a heart of a patient undergoing cardiac contractility modulation therapy by a cardiac therapy device. The method includes the steps of applying cardiac contractility modulating signals to the heart, sensing an electrical signal associated with cardiac activity of the patient, detecting in the electrical signal cardiac events associated with the cardiac activity to provide data related to the heart rate of the heart, processing the data to detect a cardiac arrhythmia, delivering anti-arrhythmic therapy to the heart of the patient if an arrhythmia is detected, providing the anti-arrhythmic therapy device with control signals associated with the delivery of the cardiac contractility modulating signals to the heart, and using the control signals to prevent electrical artifact signals associated with the delivery of the cardiac contractility modulating signals to the heart from interfering with the detecting of the cardiac arrhythmia.

Furthermore, in accordance with another preferred embodiment of the present invention, the step of using includes disabling the sensing of the electrical signal in response to a control signal associated with the delivery of a cardiac contractility modulating signal to the heart. The disabling is performed within a refractory time period. The refractory time period includes a portion of the cardiac beat cycle. The cardiac contractility modulating signal is delivered to the heart within the refractory time period.

Furthermore, in accordance with another preferred embodiment of the present invention, the step of using includes disabling the detecting of the cardiac events in the electrical signal in response to a control signal associated with the delivery of a cardiac contractility modulating signal to the heart. The disabling is performed within a refractory time period. The refractory time period includes a portion of the cardiac beat cycle. The cardiac contractility modulating signal is delivered to the heart within the refractory time period.

Furthermore, in accordance with another preferred embodiment of the present invention, the step of using includes modifying the electrical signal in response to a control signal associated with the delivery of a cardiac contractility modulating signal to the heart. The disabling is performed within a refractory time period. The refractory time period includes a portion of the cardiac beat cycle. The cardiac contractility modulating signal is delivered to the heart within the refractory time period.

Furthermore, in accordance with another preferred embodiment of the present invention, the modifying includes controllably filtering the electrical signal within the refractory time period to prevent detection of the electrical artifact signal associated with the delivery of the cardiac contractility modulating signal to the heart.

Furthermore, in accordance with another preferred embodiment of the present invention, the step of using includes filtering the electrical signal to prevent detection of the electrical artifact signals associated with the delivery of the cardiac contractility modulating signals to the heart.

Furthermore, in accordance with another preferred embodiment of the present invention, the filtering includes using a matched filter adapted for favoring detection of the cardiac events representing the beating of the heart and for rejecting frequencies characteristic to the electrical artifacts associated with the delivering of the cardiac contractility modulating signals to the heart.

Furthermore, in accordance with another preferred embodiment of the present invention, the processing includes processing the data to determine the heart rate of the heart, classifying the determined heart rate according to a classification method adapted to determine the suspected occurrence of different types of arrhythmias based on the determined heart rate, and controlling the delivery of a selected type of anti-arrhythmic therapy to the heart in response to detection of a suspected arrhythmia type.

Furthermore, in accordance with another preferred embodiment of the present invention, the processing further includes correcting or compensating for errors in the classifying of the heart rate.

Furthermore, in accordance with another preferred embodiment of the present invention, the errors include the erroneous detection of electrical artifact signals as cardiac events associated with cardiac beats. The electrical artifact signals are associated with the delivery of the of cardiac contractility modulating signals to the heart. The correcting or compensating for the errors includes subtracting the number of cardiac contractility modulating signals delivered to the heart within a time period including a number of cardiac beat cycles from the number of cardiac events detected within the duration of the time period.

Furthermore, in accordance with another preferred embodiment of the present invention, the errors include errors due to stopping of the sensing or stopping of the detecting of cardiac events within a refractory time period. The refractory time period includes a portion of the cardiac beat cycle of the heart. The errors are corrected by stopping the delivery of the cardiac contractility modulating signals to the heart when the heart rate of the heart exceeds a threshold value, and performing the classifying using the classification method in the absence of the cardiac contractility modulating signals.

Furthermore, in accordance with another preferred embodiment of the present invention, the anti-arrhythmic therapy is selected from a defibrillating shock therapy, a cardioverting shock therapy, anti-tachycardia pacing therapy, anti-bradycardia pacing therapy, variable energy shock therapy, and combinations thereof.

Furthermore, in accordance with another preferred embodiment of the present invention, the applying of cardiac contractility modulating signals to the heart is terminated prior to or upon the delivering of the anti-arrhythmic therapy to the heart of the patient.

Furthermore, in accordance with another preferred embodiment of the present invention, the applying of cardiac contractility modulating signals to the heart is renewed after the delivering of the anti-arrhythmic therapy to the heart of the patient is terminated.

Furthermore, in accordance with another preferred embodiment of the present invention, the method further includes protecting the electronic circuitry of the cardiac therapy device from high voltages generated during the applying of the anti-arrhythmic therapy to the heart.

Finally, in accordance with another preferred embodiment of the present invention, the method further includes pacing at least one chamber of the heart of the patient.

BRIEF DESCRIPTION OF THE DRAWINGS

The invention is herein described, by way of example only, with reference to the accompanying drawings, in which like components are designated by like reference numerals, wherein.

DETAILED DESCRIPTION OF THE INVENTION

The following terms are used throughout the application:

| Term | Definition |
| --- | --- |
| AC | Alternating Current |
| AGC | Automatic Gain Control |
| AICD | Automatic Internal Cardioverter Defibrillator |
| ATC | Automatic Threshold Control |
| ATP | Anti-Tachycardia Pacing |
| CCM | Cardiac Contractility Modulation |

-continued

| Term | Definition |
| --- | --- |
| CHF | Congestive Heart Failure |
| DC | Direct Current |
| ECD | External Cardiac Defibrillator |
| ETC | Excitable Tissue Control |
| ICD | Internal Cardiac Defibrillator |
| LUT | Look Up Table |
| SVT | Supra Ventricular Tachycardia |
| VF | Ventricular Fibrillation |
| VT | Ventricular Tachycardia |

Figure 1:
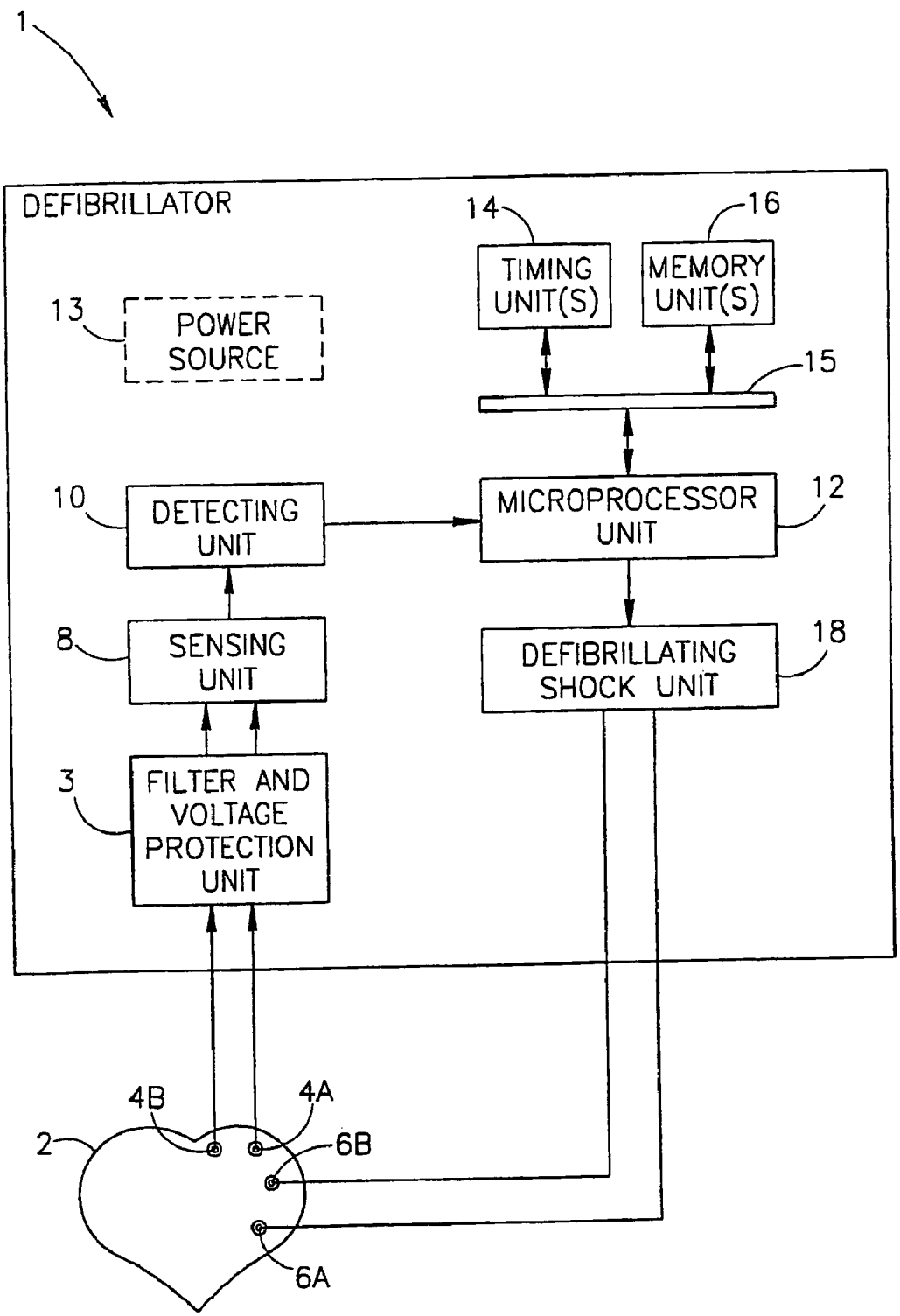
FIG. 1 is a schematic functional block diagram illustrating a prior art defibrillator device.

Reference is now made to FIG. 1 which is a schematic functional block diagram illustrating a prior art defibrillator device.

The defibrillator device 1 includes a filter and voltage protection unit 3 which is suitably electrically connected to sensing electrodes 4A and 4B which are implanted in or about the heart 2. The filter and high voltage protection unit 3 may includes various types of filtering circuitry for filtering the electrical signals sensed by the sensing electrodes 4A and 4B to remove signal components having undesirable frequencies (such as electrical noise at mains frequencies or other filterable noise) and for protecting the other circuitry of the defibrillator device 1 from high voltage signals resulting from the delivery of the electrical defibrillating shocks to the heart 2. The defibrillator 1 further includes a sensing unit 8 which is electrically connected to the filter and high voltage protecting unit 3.

The sensing unit 8 may include amplification circuitry for amplifying the filtered electrical signals. The output of the sensing unit 8 is suitably connected to a detecting circuit which performs the detection of electrical depolarization events representing cardiac activation. The detecting unit may be any analog or digital unit which is capable of detecting cardiac depolarization events by comparing it to a detection threshold as is known in the art or by any other event detection method which is known in the art. For example, the sensing unit 8 and the detecting unit 10 may be implemented using analog circuitry as disclosed by Dennis A. Brumwell et al. in Chapter 14 titled "THE AMPLIFIER: SENSING THE DEPOLARIZATION" of the book titled "IMPLANTABLE CARDIOVERTER DEFIBRILLATOR THERAPY: THE ENGINEERING-CLINICAL INTERFACE", pp. 275-302, Eds. Mark W. Kroll and Michael H. Lehmann, Kluwer Academic Publishers, USA, 1997, incorporated herein by reference. However, The sensing unit 8 and the detecting unit 10 may also be implemented by other different analog or digital circuits or any combinations thereof as is known in the art of defibrillators.

The defibrillator device 1 further includes a microprocessor unit 12 connected to the detecting unit 10 to receive therefrom signals representing the detection of cardiac depolarization events. The microprocessor unit 12 is also connected to Timing unit(s) 14 for receiving timing signals therefrom, and to memory unit(s) 16. The memory units 16 may be one or more memory devices for storing and retrieving data. The memory unit(s) 16 may include read-only memory devices and read-write memory devices for storage and retrieval of data. The timing unit(s) 14 and the memory unit(s) 16 communicate with the microprocessor unit 12 through a data bus 15.

The microprocessor 12 is also connected to a defibrillating unit 18 which is controlled by the microprocessor unit 12. The defibrillating shock unit 18 is designed to deliver electrical defibrillating shocks to the heart 2 through suitable defibrillating electrodes 6A and 6B disposed in or about the heart 2. The defibrillating shock unit 18 may typically include a current source such as a battery (not shown), a charging circuit (not shown), and high voltage output switches (not shown) as is known in the art. For example, the defibrillating shock unit 18 may be implemented as disclosed by C. G. Supino in Chapter 8 titled "THE SYSTEM", pp. 163-172 of the book titled "IMPLANTABLE CARDIOVERTER DEFIBRILLATOR THERAPY: THE ENGINEERIONG-CLINICAL INTERFACE", Eds. Mark W. Kroll and Michael H. Lehmann, Kluwer Academic Publishers, USA, 1997, incorporated herein by reference. However, the defibrillator unit 18 may be implemented using any design or circuit for delivering defibrillation shocks to the heart which is known in the art.

The defibrillator device 1 also includes a power source 13 for providing power to the various components of the device 1. The power source 13 is suitably operatively connected (connections not shown for the sake of clarity-of illustration) to provide electrical energy the components of the defibrillator device 1 as is known in the art. The power source 13 may be an electrochemical cell or a battery (primary or rechargeable), or the like but may be any other suitable power source for providing electrical power which is known in the art. It is noted that while the power source 13 is shown as included within the defibrillator device 1, the power source 13 may be also disposed externally to the device 1. For example, the power source 13 may be a power source such as, but not limited to, a conditioned or regulated DC or AC power supply, operatively connected to the mains power supply (not shown) as is known in the art. Such mains powered external defibrillator devices are well known in the art.

It is noted that the defibrillator device 1 of FIG. 1 is given herein by way of a non-limiting example of a prior art defibrillator and that many other types of defibrillators using different hardware implementations are possible as is known in the art.

The defibrillator device 1 represents an automatic implantable defibrillator device (AICD). However, other types of defibrillators such as external cardiac defibrillator (ECD) devices are also known in the art.

In operation, the sensing unit 8 amplifies the filtered electrical signals sensed by the sensing electrodes 4A and 4B, the detecting unit 10 receives the amplified filtered signals and detects depolarization events, the detection may employ various methods such as threshold crossing detection methods as disclosed by Brumwell et al., including, but not limited to, AGC methods and ATC methods. However any other suitable event detection methods known in the art may also be used for event detection. The detecting unit 10 provides to the microprocessor unit 12 detection signals representative of the detection of an event in the sensed amplified signal provided by the sensing unit 8. The microprocessor unit 12 processes the detection signals using suitable processing programs embedded in the microprocessor unit 12 or in the memory unit(s) 16 connected thereto. The various processing algorithms are generally referred to as classification algorithms or classification programs. The classification programs process the temporal data of the time of occurrence of the detection signals and classify the sensed cardiac rhythm as belonging to one of a plurality of possible cardiac rhythm categories. In a non-limiting example, the categories may include a range of heart rates defined as normal cardiac rate for a particular patient, an elevated heart rate range classified as a ventricular tachycardia (VT), and another elevated heart rate range classified as a ventricular fibrillation (VF). The various classification methods and algorithms are well known in the art are not the subject matter of the present invention and will therefore not be disclosed in detail hereinafter. Some exemplary methods of tachy-arrhythmia detection methods are disclosed by Stan M. Bach et al. in Chapter 15, titled "TACHYARRHYTHMIA DETECTION", pp. 303-323, of the book titled "IMPLANTABLE CARDIOVERTER DEFIBRILLATOR THERAPY: THE ENGINEERING-CLINICAL INTERFACE", Eds. Mark W. Kroll and Michael H. Lehmann, Kluwer Academic Publishers, USA, 1997, incorporated herein by reference.

If a VF episode is detected, the microprocessor unit 12 may, based on such a detection, outputs various control signals to the defibrillating shock unit 18 for initiating the charging of a high voltage capacitor (not shown) included in the defibrillating unit 18 in preparation for delivering a defibrillation shock to the heart. After verification of the detection of VF, further control signals, sent from the microprocessor unit 12 to the defibrillating unit 18, may initiate the delivering of a defibrillating shock to the heart 2.

Some prior art defibrillator/cardioverter devices are also capable of delivering Anti-tachycardia pacing (ATP) and cardioversion therapy after detection of VT, as is well known in the art. For example, such devices and methods of delivering ATP and cardioversion therapy are disclosed in Chapter 16, titled "ANTI-TACHYCARDIA PACING AND CARDIOVERSION" pp. 325-342, of the book titled "IMPLANTABLE CARDIOVERTER DEFIBRILLATOR THERAPY: THE ENGINEERING-CLINICAL INTERFACE", Eds. Mark W. Kroll and Michael H. Lehmann, Kluwer Academic Publishers, USA, 1997, incorporated herein by reference. Such devices may utilize pacing circuitry (not shown in FIG. 1 for the sake of clarity of illustration) to deliver various pacing and shock signals to the heart for treating the ventricular tachycardia.

It is noted that the term Anti-arrhythmic devices is used throughout the present application to indicate devices for delivering anti-arrhythmia therapy to the heart, the anti-arrhythmia therapy may include defibrillating shocks suitable for VF termination, anti-arrhythmic pacing therapy suitable for treating tachy-arrhythmias such as supra-ventricular tachycardia (SVT) and other types of ventricular tachycardia (VT), cardioversion therapy, and any combination of the above therapies with pacing pulses for anti-bradycardia therapy.

Figure 2:
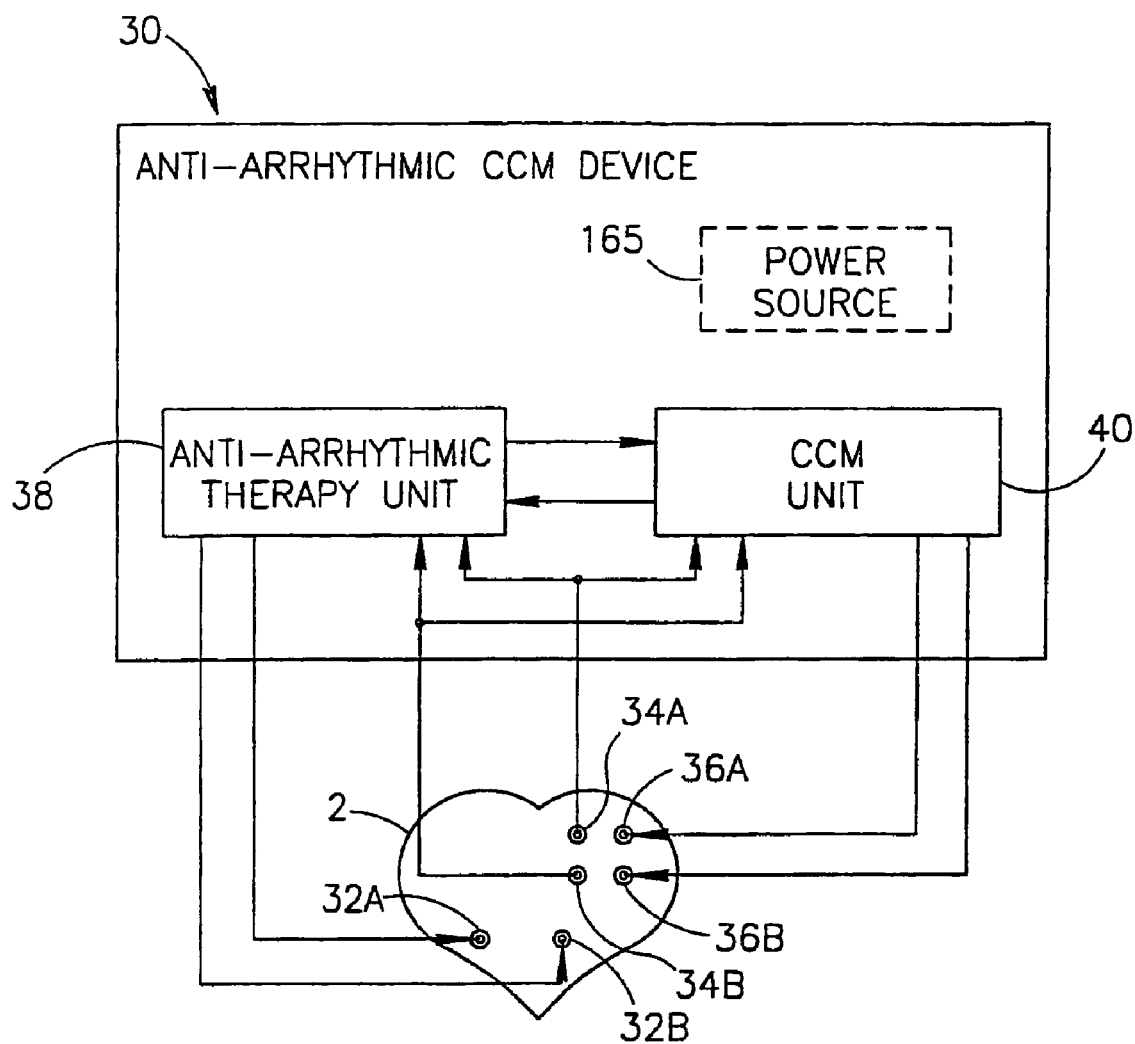
FIG. 2 is a schematic diagram illustrating a cardiac contractility modulating device having anti-arrhythmic therapy capabilities, in accordance with a preferred embodiment of the present invention.

Reference is now made to FIG. 2 which is a schematic diagram illustrating a cardiac contractility modulating device having anti-arrhythmic therapy capabilities, in accordance with a preferred embodiment of the present invention.

The anti-arrhythmic CCM device 30 includes an anti-arrhythmic therapy unit 38 and an a CCM unit 40. The anti-arrhythmic therapy unit 38 is operatively connected to the CCM unit 40 for receiving control signals therefrom. The anti-arrhythmic therapy unit 38 is connectable to sensing electrodes 34A and 34B for sensing cardiac depolarization events as disclosed hereinabove for prior art defibrillating devices. The anti-arrhythmic therapy unit 38 is also connectable to a pair of therapy delivering electrodes 32A and 32B, for delivering anti-tachycardia therapy to the heart 2 through the electrodes 32A and 32B as is known in the art and disclosed hereinabove. The anti-arrhythmic CCM device 30 also includes a power source 165 for providing power to the various components of the anti-arrhythmic CCM device 30. The power source 165 is suitably operatively connected to the various components of the anti-arrhythmic CCM device 30 (connections not shown for the sake of clarity of illustration) to provide electrical energy the components of the anti-arrhythmic CCM device 30, as is known in the art. The power source 165 may be an electrochemical cell or a battery (primary or rechargeable), or the like but may be any other suitable power source for providing electrical power which is known in the art. It is noted that while the power source 165 is shown as included within the anti-arrhythmic CCM device 30, the power source 165 may be also disposed externally to the anti-arrhythmic CCM device 30. For example, the power source 165 may be a power source such as, but not limited to, a conditioned or regulated DC or AC power supply, operatively connected to the mains power supply (not shown), as is known in the art.

For example, in accordance with one preferred embodiment of the present invention, the anti-arrhythmic therapy unit 38 is a defibrillating shock unit and the electrodes 32A and 32B are defibrillation electrodes suitable for delivering defibrillating shocks to the heart 2, as is known in the art and disclosed hereinabove.

Alternatively, in accordance with another preferred embodiment of the present invention, the anti-arrhythmic therapy unit 38 is an energy cardioverting shock unit and the electrodes 32A and 32B are cardiovertion electrodes suitable for delivering cardioverting shocks to the heart 2, as is known in the art and disclosed hereinabove.

In accordance with yet another preferred embodiment of the present invention, the anti-arrhythmic therapy unit 38 is a unit capable of delivering anti-tachycardia pacing (ATP) therapy and the electrodes 32A and 32B are pacing electrodes suitable for delivering ATP therapy pulses to the heart 2, as is known in the art and disclosed hereinabove.

Furthermore, accordance with yet another preferred embodiment of the present invention, the anti-arrhythmic therapy unit 38 is a multi-modal anti-arrhythmic therapy unit capable of delivering cardioverting shock therapy, anti-tachycardia pacing (ATP) therapy, and defibrillating shock therapy. In such a case, more than one pair of therapy delivering electrodes (not shown) may need to be connected to the anti-arrhythmic therapy unit 38. For example, the electrodes 32A and 32B may be pacing electrodes suitable for delivering ATP therapy pulses to the heart 2, as is known in the art and disclosed hereinabove, and additional electrodes (not shown) or electrodes pairs (not shown) may be suitably connected to the anti-arrhythmic therapy unit 38, such as defibrillating electrodes (not shown) and/or defibrillating/cardioverting electrodes (not shown).

The CCM unit 40 is connectable to a pair of CCM electrodes 36A and 36B (also known as ETC electrodes) and is capable of delivering CCM signals (also known in the art as ETC signals) to the heart through the CCM electrodes 36A and 36B to modulate cardiac contractility as disclosed by Ben Haim et al. and by Mika et al. in the PCT publications and applications and in the Co-pending patent applications referenced hereinabove. It is noted that, the anti-arrhythmic therapy unit 38 may be any anti-arrhythmia therapy device known in the art and may be implemented as an analog unit, a digital unit or a hybrid analog and digital unit.

It will be appreciated by those skilled in the art that the anti-arrhythmic CCM device 30 of FIG. 2 may also be adapted to include a pacing unit (not shown). Such a pacing unit may be used in conjunction with suitable pacing electrodes (not shown) for pacing the heart 2, for example, in patients in need of anti-bradycardia pacing. Additionally, the pacing unit (not shown) may be integrated in the anti-arrhythmic therapy unit 38 such that it may be used for delivering ATP therapy if the need for such therapy is detected by the anti-arrhythmic therapy unit 38, as is known in the art and disclosed in U.S. Pat. No. 4,830,006 to Haluska et al.

It is noted that while the anti-arrhythmic therapy unit 38, is illustrated as being connected to a single pair of sensing electrodes 34A and 34B, a single pair of electrodes 32A and 32B for delivering anti-tachycardia therapy to the heart 2, and a single pair of CCM electrodes for delivery of CCM signals to the heart 2, many other electrode configurations and combinations are possible which are all considered to be within the scope of the present invention. For example, the anti-arrhythmic therapy unit 38 may be connected to more than one CCM delivering electrode pair or electrodes (not shown) for delivering CCM signals to more than one cardiac region. In another example, more than one pair of sensing electrodes or a plurality of single sensing electrodes (not shown) may be used for enabling multi chamber sensing and/or pacing, such multi-electrode configurations are disclosed in the above referenced, PCT publications to Ben Haim et al. and in co-pending U.S. patent applications Ser. Nos. 09/276,460, 09/328,068 and 09/338,649 to Mika et al., and in the corresponding PCT applications.

It is noted that many types of sensing electrodes, pacing electrodes, shock therapy delivering electrodes may be used in conjunction with the anti-arrhythmic CCM device 38 of FIG. 2. Such electrodes are known in the art and may also be commercially obtained. The electrode types have to be suitably adapted to the design and implementation of the device anti-arrhythmic CCM device 38. For example if the device 38 is adapted for use in an intensive care unit it may use epicardial electrodes or other external types of electrodes. In chronically implanted devices, the electrodes may be intracardiac electrodes adapted for sensing, pacing, defibrillation shock delivery electrodes or any other types of anti-arrhythmia therapy electrodes known in the art.

Preferably, the anti-arrhythmic therapy unit 38 and the CCM unit are both in communication with a common microprocessor unit (not shown in FIG. 2, for the sake of clarity of illustration). In such a case, the microprocessor unit (not shown) controls the delivery of CCM signals by the CCM unit 40 and also sends control signals to the anti-arrhythmic therapy unit 38. The control signals sent from the microprocessor unit (not shown) control the anti-arrhythmic therapy unit 38 to prevent the CCM signal induced electrical artifacts from interfering with the detection of cardiac arrhythmias as is disclosed in detail hereinafter. Alternatively, the anti-arrhythmic therapy unit 38 and the CCM unit 40 may each include a dedicated microprocessor unit (the microprocessor units are not shown in FIG. 2, for the sake of clarity of illustration). In the latter case the microprocessor unit (not shown) of the anti-arrhythmic therapy unit 38 is in communication with the microprocessor unit (not shown) of the CCM unit 40 to provide the microprocessor unit of the anti-arrhythmic therapy unit 38 with data representative of the time of delivery of CCM signals by the CCM unit 40. This data is processed by the microprocessor of the anti-arrhythmic therapy unit 38, or by the microprocessor of the CCM unit 40 or by both of these microprocessors to prevent the interference of the CCM signal induced electrical artifacts from interfering with the detection of cardiac arrhythmias as is disclosed in detail hereinafter.

Briefly, in accordance with a preferred embodiment of the present invention the control signals may be used to prevent the sensing of CCM signal induced artifacts at the sensing level.

In accordance with another preferred embodiment of the present invention the control signals may be used to prevent the sensing of CCM signal induced artifacts at the detecting level.

In accordance with yet another preferred embodiment of the present invention the control signals may be used to prevent the sensing of CCM signal induced artifacts at the sensing and the detecting level simultaneously.

Alternatively, In accordance with yet another preferred embodiment of the present invention the control signals may be used to prevent the CCM signal induced electrical artifacts from interfering with the detection of cardiac arrhythmias, not by preventing the sensing or the detecting of the CCM signal induced electrical artifact but by correcting or compensating the error introduced by detection of the CCM induced artifacts as cardiac events at the arrhythmia classification program level. This correction or compensation is achieved computationally by suitably processing the control signals indicative of the delivery of an ETC signal.

In operation, the CCM unit 40 may operate to deliver CCM signals to the heart through the CCM electrodes 36A and 36B or through any other pair (not shown) or pairs (not shown) of electrodes applied to more than one cardiac site. The pair of sensing electrodes 34A and 34B may be commonly used for feeding the sensed signals to the sensing unit (not shown) of the anti-arrhythmic therapy unit 38 and to the sensing unit (not shown) of the CCM unit 40. Alternatively, different separate pairs of electrodes (not shown) may be used for sensing by each of the anti-arrhythmic therapy unit 38 and the CCM unit 40. Prior to the delivery of CCM signals to the heart 2, the CCM unit 40 or the microprocessor (not shown in FIG. 2) which controls the CCM unit 40 delivers control signals to the anti-arrhythmic therapy unit 38. These control signal are related to the delivery of the CCM signals and are used by the anti-arrhythmic therapy unit 38 to disable the sensing of the CCM related electrical artifacts or to disable the detection of these artifacts as cardiac depolarization events.

It is noted that, additional control signals may also be delivered to the anti-arrhythmic therapy unit 38 during the delivery of a CCM signal to the heart if the method of filtering the artifact signal is employed at the level of a signal filtering unit (not shown) as is disclosed in more detail hereinafter.

Figure 3:
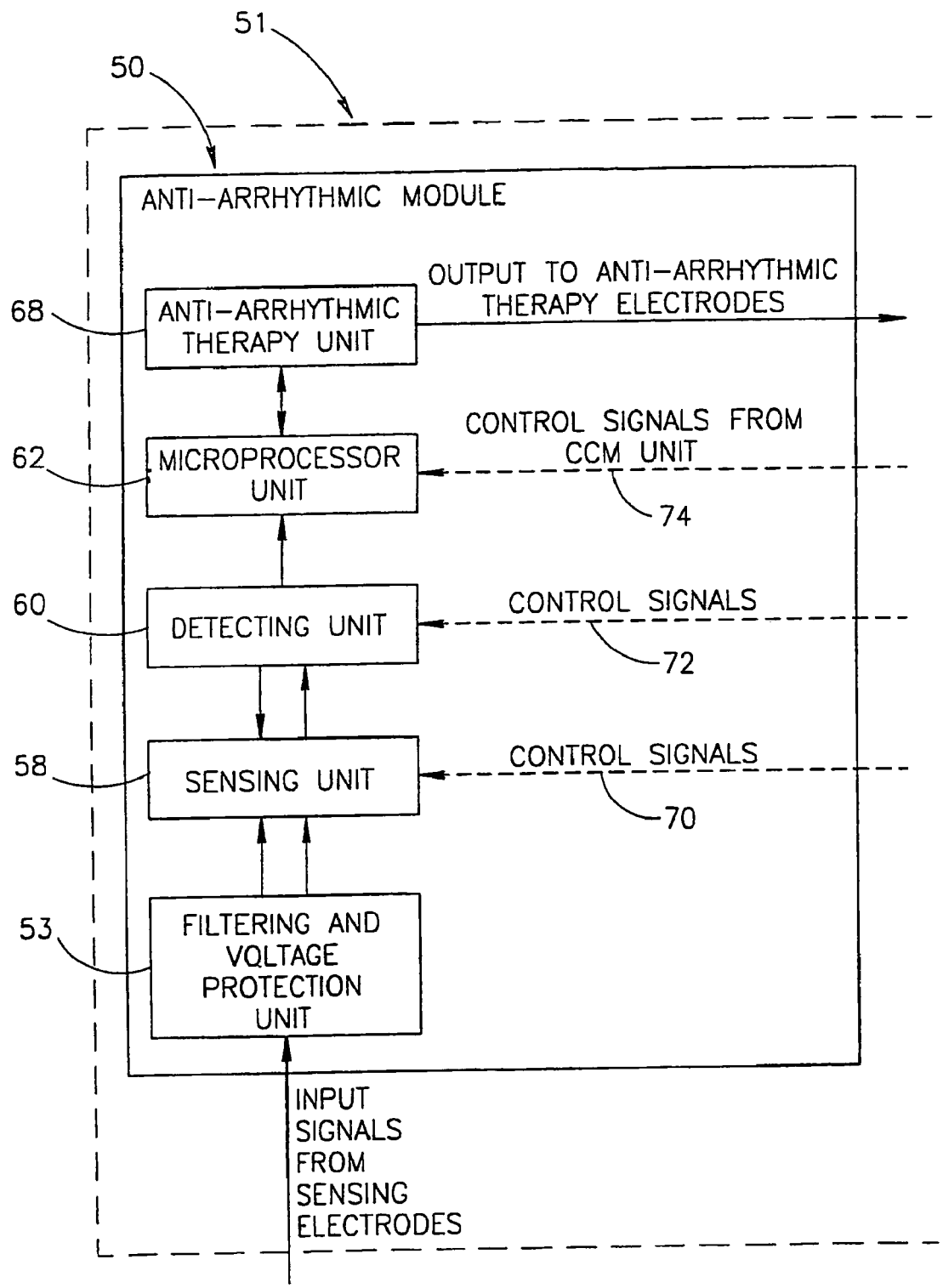
FIG. 3 is a schematic diagram illustrating a detail of a cardiac contractility modulating device having anti-arrhythmic therapy capabilities, useful in understanding possible implementation methods of control signals at different levels of a part of the cardiac contractility modulating device of the present invention.

Reference is now made to FIG. 3 which is a schematic diagram illustrating a detail of a cardiac contractility modulating device having anti-arrhythmic therapy capabilities, useful in understanding possible implementation methods of control signals at different levels of a part of the cardiac contractility modulating device of the present invention.

In FIG. 3, an anti-arrhythmic module 50 is illustrated which is integrated within a CCM anti-arrhythmic device 51 (only a part of the device 51 is shown, for the sake of clarity of illustration). The module 50 includes a filtering and voltage protection unit 53, which receives input signals from sensing electrodes (not shown) disposed in or about the heart and is connected to a sensing unit 58. The filtering and voltage protection unit 53 is operative to filter the signals from the sensing electrodes and to protect the sensing unit 58 connected thereto from the high energy defibrillating shock related signals, as is known in the art and disclosed hereinabove.

The sensing unit 58 amplifies the signal received from the sensing electrodes (not shown) The sensing unit 58 is connected to a detecting unit 60 which detects depolarization events in the filtered amplified signals at the output of the sensing unit 58 as disclosed in detail hereinabove for the prior art defibrillator 1 of FIG. 1. The detecting unit 60 is operatively connected to a microprocessor unit 62.

The microprocessor unit 62 is operatively connected to an anti-arrhythmic therapy unit 68 and controls the delivery of anti-arrhythmic therapy signals to the heart 2 by controlling the output of anti-arrhythmic therapy signals from anti-arrhythmic therapy unit 68. The anti-arrhythmic therapy unit 68 may be any type of device or unit known in the art for delivering one or more anti-arrhythmic type of therapy to the heart. For example, the anti-arrhythmic therapy unit 68 may be a defibrillator unit, a cardioverter/defibrillator unit, or a multi-modal cardiac therapy unit similar to the cardiac stimulator disclosed by Haluska et al. in U.S. Pat. No. 4,830,006, or any other type of anti-arrhythmic therapy unit known in the art.

The anti-arrhythmic module 50 receives control signals from other parts (not shown in detail) of the CCM device 51 within which it is integrated. The control signals may be received from the CCM unit (not shown) which is also integrated within the CCM device 51, or from a microprocessor or controller unit (not shown) which is included in or communicating with the CCM unit (not shown). Alternatively, the microprocessor unit 62 may control the entire CCM device 51, including the CCM unit (not shown).

The prevention of interference of the sensed CCM signal induced electrical artifacts may be implemented in various ways. In accordance with one preferred embodiment of the present invention, the prevention of interference is implemented at the sensing level. In this implementation, suitable control signals are sent to the sensing unit 58 prior to the delivery of each CCM signal to the heart 2. These control signals are represented by the dashed arrow 70. Each of the received control signals causes the sensing unit 58 to become refractory to incoming input signals from the filtering and voltage protecting unit 53. The timing and duration of the control signals are such that the sensing unit 58 becomes refractory to incoming input signals before the delivery of the CCM signal to the heart and stays refractory for a refractory period having a duration that is sufficient to prevent the CCM induced electrical artifact from being detected as an event by the detection unit 60. Thus, the refractory period of the sensing unit 58 may last longer than the duration of the CCM signal delivered to the heart, to accommodate for the precise shape, amplitude, polarity and duration of the CCM induced artifact as it is sensed by the sensing unit 58. The duration of the refractory period may be a fixed duration, or may be a preset duration that may be programmed, telemetrically or non-telemetrically, into the memory (not shown) of the CCM device 51 based on actual determination of the artifact parameters obtained from each individual patient in a recording and measurement session taking place after implantation of the electrodes in the patient.

Thus, the determination of the duration of the refractory period is done such as to take into account the maximal duration of CCM signal induced electrical artifact which may be picked up by the sensing electrodes (not shown) and is capable of being erroneously detected as a true event in the patient in which the device 51 is operative. This maximal duration is preferably determined empirically for each patient by a physician or cardiologist after collecting data in a test session of the device 51 in the patient taking place after electrode implantation. It is also preferred to add a certain safety margin by increasing the refractory period above the value of the empirically determined maximal duration, this safety margin may be advantageous in preventing erroneous event detection in cases in which the CCM signal induced electrical artifact has large variability or may show drift over extended periods of time due to electrode movements or other reasons.

It is noted that some CCM devices may apply to the heart of the same patient different types of CCM signals having different or varying signal parameters, in response to different cardiac conditions or for changing and controlling the contractility and cardiac output of the heart. The CCM signal parameters that may vary include, but are not limited to, CCM signal amplitude, CCM signal duration, CCM signal waveform, and CCM signal polarity.

Thus, if the refractory period duration is a fixed duration, care must be taken to select such a duration that is long enough to ensure that any type of CCM signal which the device 51 is capable of delivering to the heart will not result in erroneous (spurious) detection of the CCM signal induced electrical artifact as a detected event. Alternatively, the refractory period may be a variable refractory period and the device 51 may be adapted to select a particular value of a refractory period duration from a preprogrammed look up table (LUT), which includes different refractory period duration values associated with different CCM signal types. The data in the LUT may be obtained by empirical tests performed in the patient in a testing or data collection session after implantation of the electrodes in each individual patient. Such tests may record the parameters of the electrical artifacts associated with the delivery of cardiac contractility modulating signals having different parameters. The parameters of the recorded electrical artifacts may then be used to determine appropriate refractory period parameter sets for each different type of deliverable CCM signal to prevent erroneous detection of the electrical artifacts as cardiac events, as disclosed in detail hereinabove. This method has the advantage of being individually adapted to each patient, and of enabling the control of the refractory period on a beat by beat basis.

The sensing unit 58 may receive the control signals from the microprocessor unit which controls the activation of the CCM unit. In the embodiment in which the device 51 includes only one microprocessor unit 62, the sensing unit 58 receives the control signals from the microprocessor unit 62. If the CCM unit (not shown) of the device 51 is controlled by a second microprocessor or controller (not shown) which is not the microprocessor 62, the control signals for controlling the refractory period of the sensing unit 58 may be received from the second microprocessor or controller.

In accordance with another preferred embodiment of the present invention, the prevention of interference is implemented at the detecting level. In this implementation, suitable control signals are sent to the detecting unit 60 prior to the delivery of each CCM signal to the heart 2. These control signals are represented by the dashed arrow 72. Each received control signal causes the detecting unit 60 to become refractory to incoming input signals from the sensing unit 58. The timing and duration of the control signals are such that the detecting unit 60 becomes refractory to incoming input signals before the delivery of the CCM signal to the heart and stays refractory for a refractory period having a duration that is sufficient to prevent the CCM induced electrical artifact from being detected as an event by the detection unit 60. Thus, the refractory period of the detecting unit 60 may last longer than the duration of the CCM signal delivered to the heart, to accommodate for the precise shape, amplitude and duration of the CCM induced artifact as it is sensed by the sensing unit 58. The duration of the refractory period of detecting unit 60 may be a fixed duration, or may be a preset duration that may be programmed, telemetrically or non-telemetrically, into the memory (not shown) of the device 51 based on actual determination of the maximal artifact parameters obtained from each individual patient in a recording and measurement session taking place after implantation of the electrodes in the patient.

Similar to the refractory period of the sensing unit 58 disclosed hereinabove, if the refractory period duration of the detecting unit 60 is a fixed duration, care must be taken to select such a duration that is long enough to ensure that any type of CCM signal which the device 51 is capable of delivering to the heart will not result in erroneous (spurious) detection of the CCM signal induced electrical artifact as a detected event. Alternatively, the refractory period of the detecting unit 60 may be a variable refractory period and the device 51 may be adapted to select a particular value of a refractory period duration from a preprogrammed look up table (LUT) which includes different refractory period duration values associated with different CCM signal types. The data in the LUT may be obtained by empirical tests performed in the patient in a testing or data collection session after implantation of the electrodes in each individual patient.

Such tests may record the parameters of the electrical artifacts associated with the delivery of cardiac contractility modulating signals having different parameters. The parameters of the recorded electrical artifacts may then be used to determine appropriate refractory period parameter sets for each different type of deliverable CCM signal to prevent erroneous detection of the electrical artifacts as cardiac events, as disclosed in detail hereinabove. This method has the advantage of being individually adapted to each patient, and of enabling the control of the refractory period on a beat by beat basis. The method is adapted for use in CCM devices which are capable of delivering variable CCM signals and of adapting one or more of the CCM signal parameters (such as but not limited to the amplitude, duration, wave shape, and polarity of the CCM signal) for controlling the effect of the CCM signals on the cardiac contractility and/or on the cardiac output. In accordance with a preferred embodiment of the present invention, since in such CCM devices, the CCM signals parameters may be varied in time according to, inter alia, detected patient need and patient metabolic state, the microprocessor unit 62 may select from the LUT the appropriate refractory period parameters which are associated with the parameters of the particular CCM signal which is about to be delivered to the heart of the patient under the control of the microprocessor unit 62. This method has the advantage of being individually adapted to each patient and of flexibly and automatically allowing the selection of refractory period duration which is adapted to the parameters of the currently delivered CCM signal parameters, thus, allowing control of CCM signal parameters while still efficiently preventing erroneous detection of the CCM induced electrical artifacts as true events.

The detecting unit 60 may receive the control signals from the microprocessor unit which controls the activation of the CCM unit. In the embodiment in which the device 51 includes only one microprocessor unit 62, the detecting unit 60 receives the control signals from the microprocessor unit 62. If the CCM unit (not shown) of the device 51 is controlled by a second microprocessor or controller (not shown) which is not the microprocessor 62, the control signals for controlling the refractory period of the detection unit 60 may be received from the second microprocessor or controller.

It is noted that, the microprocessor unit 62 may be a microprocessor unit which is dedicated to the module 50 or may be a microprocessor unit which is commonly used to control the operation of the entire CCM device 51.

Furthermore, in accordance with another preferred embodiment of the present invention, the control signals may cause the sensing unit 58 and the detecting unit 60 to become refractory as disclosed hereinabove. This implementation has the advantage that more power is conserved by putting both the sensing unit 58 and the detecting unit 60 into a refractory state since the power consumption of each of these units is smaller in the refractory period, resulting in increasing the useful life of the battery (not Shown) or power source (not shown) which powers the device 51.

It is further noted that the preventing of the sensing and/or the detecting of CCM induced electrical artifacts as event may also be achieved by controlling the filtering and voltage protection unit 53 such as by putting it into a refractory period or by suitably controlling the filtering properties thereof such that all the signals fed into the sensing unit 58 including the CCM related electrical artifact signals are strongly attenuated during a period equivalent to the duration of the above disclosed refractory period. If the method of preventing the sensing and/or the detecting of CCM induced electrical artifacts as true events is achieved by controlling the filtering characteristics such as but not limited to the frequency response characteristics of the filtering and voltage protection unit 53, the microprocessor unit 62 which controls the filtering and voltage protection unit 53 and/or the CCM unit (not shown) of the device 51 may also provide the filtering and voltage protection unit 53 with data related to the CCM signal parameters, such as but not limited to CCM signal amplitude, CCM signal duration, CCM signal waveform, and CCM signal polarity. This CCM signal parameter related data may be provided by the microprocessor unit 62 to the filtering and voltage protection unit 53 before and/or during the time of delivery of the CCM signals to the heart. The CCM signal parameter related data is useful particularly in cases where one or more of the parameters of the CCM signals is dynamically varied under control of the microprocessor 62, during the delivery of CCM therapy, because such CCM signal parameter related data allows the control of the filtering characteristics of the filtering and voltage protection unit 53 on a beat by beat basis for CCM signals having dynamically variable parameters.

It is noted that the filtering and voltage protection unit 53 may be adapted to function as a controlled matched filter which is adapted to reject the CCM signal induced electrical artifact based on a fixed or dynamically varying template or data adapted for maximal rejection of the predicted waveform and/or frequency content of the CCM induced electrical artifact. Such template or data may be supplied to the filtering and voltage protection unit 53 by the microprocessor 62 in accordance with the data of the type and parameters of the CCM signal scheduled to be delivered to the heart in accordance with the CCM delivery control program operative on the microprocessor unit 62.

In accordance with still another preferred embodiment of the present invention, the prevention of interference of the CCM induced electrical artifact signals is implemented at the classification level. In this implementation, the sensing unit 58 and the detecting unit 60 are not put into a CCM signal related refractory period. The microprocessor 62 may receive control signals represented by the dashed arrow 74 from the CCM unit. These control signals are indicative of the timing of delivery of the CCM signals to the heart. Alternatively, in cases wherein the microprocessor 62 also controls the activation of the CCM unit (not shown) of the device 51, the microprocessor 62 has internal data therewithin indicative of the computed timing of activation of the CCM unit. In both of these alternatives the microprocessor unit 62 uses the data indicative of the timing of the delivery of CCM signals for computationally correcting or compensating for the possible errors in computing the heart rate which may be induced by spurious detection of the CCM signal induced artifact as "true" depolarization events. In a non-limiting example, the classification program may subtract the known number of CCM signals delivered to the heart within a certain number of cardiac beat cycles from the total number of events detected by the detecting unit 60 within the same beat cycles, preventing possible heart rate classification errors which may have been introduced by an erroneous number of detected events, had the correction not been applied.

It will be appreciated that the correction methods which may be used for correcting or compensating for erroneous event detection prior to processing the data for classification and arrhythmia detection must be adapted to the specific methods, programs and algorithms which are used for processing the event detection data and for the classification of heart rates for arrhythmia detection and classification.

It is noted that, while the method of triggering or inducing a refractory period in one or more of the sensing unit 58, the filtering and voltage protection unit 53 and the detecting unit 60 may provide an adequate solution to the problem of erroneous CCM induced artifact detection, care must be taken to ensure that the blanking of one or more of the sensing unit 58, the filtering and voltage protection unit 53 and the detecting unit 60 during the imposed refractory period will not by itself produce undesirable errors in the estimation of the heart rate due to the cessation of detection of any electrical events within the imposed refractory period duration. Typically, the CCM signal duration may vary between approximately 20-50 milliseconds (although lower or higher duration values may also be used). Some VT episodes in human cardiac patients may exhibit R-R intervals of approximately 250-300 millisecond duration, Therefore, when the above disclosed refractory period method is used, the blanking or refractory period may occupy approximately 20% of the total beat cycle. Thus, there is a possibility that a true event may occur within the refractory period and will therefore not be detected, which may cause errors in the determination of the heart rate. Such errors may eventually lead to wrong classification of the heart rate by the classification methods or classification algorithms used and may also undesirably delay or in extreme cases even prevent the delivery of the proper anti-arrhythmic therapy by the anti-arrhythmic module 50 of the device 51. For example, under such circumstances, an episode of VT may be missed of misclassified as allowable tachycardia, and VF may be misclassified as VT leading to delay in delivery of the proper type of anti-arrhythmic therapy or to failure to deliver any tachyarrhythmic therapy.

In order to prevent or at least to reduce the probability of the misclassification and the resulting delay or failure of the proper application of anti-arrhythmic therapy, the device 51 may be adapted to use a threshold based method to disable the delivery of CCM signals to the heart when the detected heart rate exceeds a certain threshold. Thus, in accordance with another preferred embodiment of the present invention, the device 51 continuously determines the heart rate and classifies the heart rate, in accordance with any sensing, detecting, and anti-arrhythmic heart rate classification methods or algorithms known in the art. Simultaneously, the CCM unit or circuitry operates to detect the need for CCM therapy and to control the delivery of CCM signals to the heart, in accordance with any of the methods of CCM signal delivery known in the art or disclosed in any of the above referenced published or co-pending patent applications disclosed hereinabove. If the heart rate exceeds a certain threshold level, this is classified as a suspected tachy-arrhythmia and the microprocessor 62 disables the delivery of CCM signals to the heart within a time period which is referred to as the "CCM signal free" period, hereinafter. The device 51 then continues to determine the heart rate within this CCM signal free period, in the absence of CCM signal delivery. The device 51 analyzes and classifies the heart rate in accordance with the classification criteria based on the detection data obtained by the device 51 during the CCM signal free period. The device 51 then determines whether any type of anti-arrhythmia therapy is to be delivered to the heart based on the classification of the heart rate obtained in the CCM free period.

If the classification of the heart rate obtained in the CCM free period indicates the need to deliver any type of anti-arrhythmic therapy, the device 51 continues the disabling of CCM signal delivery and initiates the delivery of the required anti-arrhythmic therapy, and continues to deliver any indicated anti-arrhythmic therapy and to determine the heart rate as is known in the art until the anti-arrhythmic therapy is terminated. If the anti-arrhythmic therapy is terminated by the device 51, the device 51 enables the delivery of CCM signals to the heart.

If the classification of the heart rate obtained in the CCM free period does not indicate a need to deliver any type of anti-arrhythmic therapy, the device 51 enables the delivery of CCM signals.

Thus, in the above disclosed method of operation of the device 51, the anti-arrhythmic detection and classification program, sub-routine or algorithm takes priority over the CCM delivery control program, sub-routine or algorithm, enabling it to override, interrupt or disable the CCM signal delivery even under conditions in which the delivery of CCM signals is called for by the CCM delivery control program to modify cardiac contractility and or cardiac output.

Figure 4:
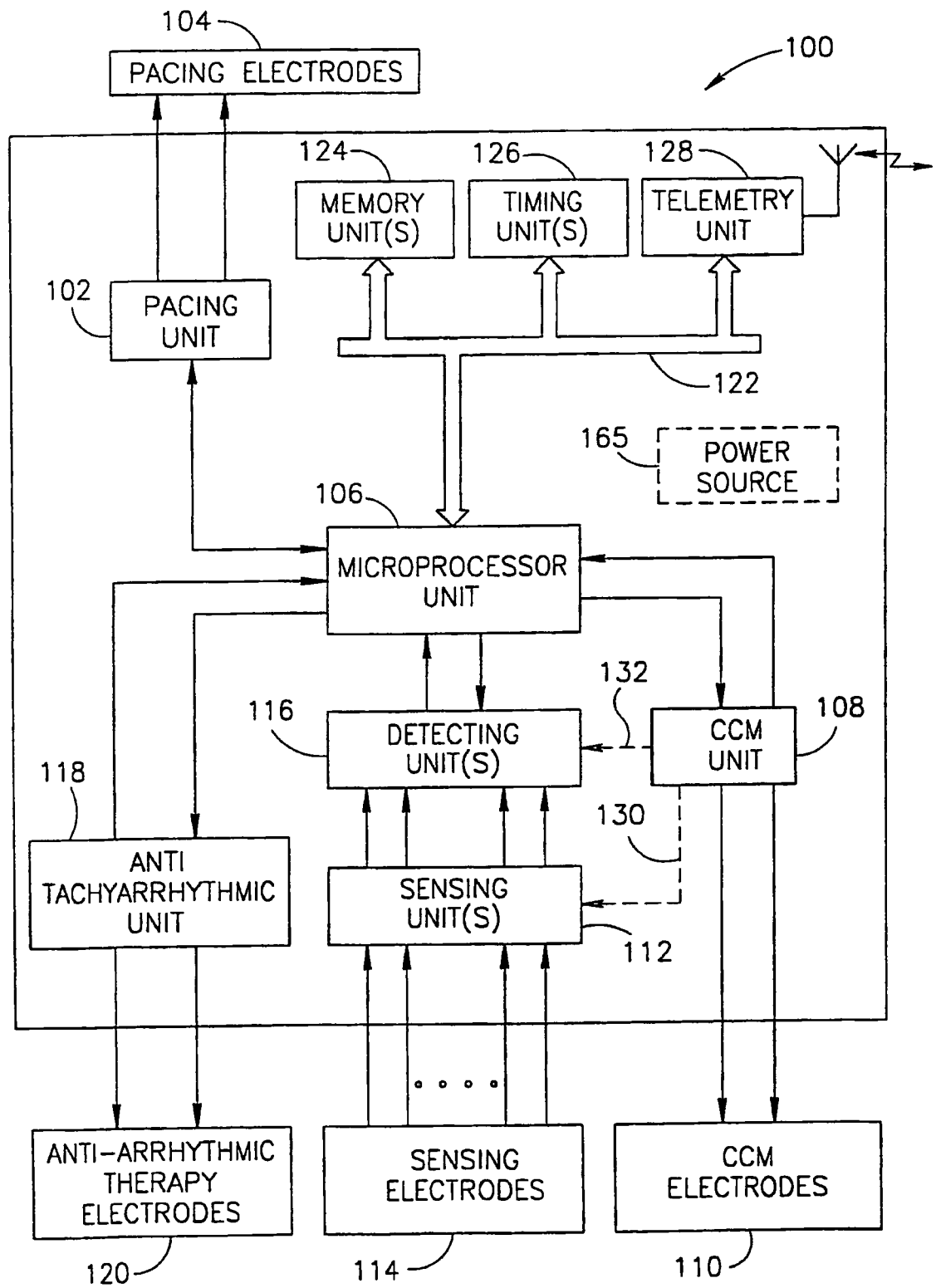
FIG. 4 is a schematic diagram illustrating a CCM device having capability of applying a plurality of different anti-arrhythmic therapy methods to the heart, in accordance with another preferred embodiment of the present invention.

Reference is now made to FIG. 4 which is a schematic diagram illustrating a CCM device having capability of applying a plurality of different anti-arrhythmic therapy methods to the heart.

The CCM device 100 of FIG. 4 includes a pacing unit 102 connectable to one or more pacing electrodes 104. The pacing unit 102 is suitably connected to a microprocessor or controller 106. The microprocessor 106 controls the pacing unit 102 to deliver pacing pulses to the heart (nor shown) for performing anti-bradycardia pacing if necessary, as is well known in the art. The CCM device 100 also includes a CCM unit 108 capable of delivering CCM signals (also known in the art as ETC signals). The CCM unit 108 is connectable to one or more CCM electrodes 110 for delivering CCM signals to the heart. The CCM device 100 also includes sensing units 112 connectable to one or more sensing electrodes 114 for sensing electrical signals at or about the heart. The CCM device 100 also includes one or more detecting units 116 which are connected to the sensing unit(s) 112 for receiving amplified sensed signals therefrom and to the microprocessor 106 for providing control signals thereto indicative of detecting depolarization events in the heart. The CCM device 100 also includes an anti-tachyarrhythmic unit 118 which is connected to the microprocessor 106 for receiving control signals therefrom. The anti-tachyarrhythmic unit 118 is connectable to one or more anti-arrhythmic therapy electrodes 120 for delivering anti-arrhythmic therapy to the heart.

The device 100 also includes a power source 165 for providing power to the various components of the device 100. The power source 165 is suitably operatively connected (connections not shown for the sake of clarity of illustration) to provide electrical energy the components of the device 100 as is known in the art. The power source 165 may be an electrochemical cell or a battery (primary or rechargeable), or the like, but may also be any other suitable power source for providing electrical power which is known in the art. It is noted that while the-power source 165 is shown as included within the device 100, the power source 165 may be also disposed externally to the device 100. For example, the power source 165 may be a power source such as, but not limited to, a conditioned or regulated DC or AC power supply, operatively connected to the mains power supply (not shown) as is known in the art.

The microprocessor unit 106 controls the output of anti-arrhythmic therapy signals from the anti-tachyarrhythmic unit 118. The anti-tachyarrhythmic unit 118 may be any type of device or unit known in the art for delivering one or more anti-arrhythmic type of therapy to the heart. For example, the anti-arrhythmic therapy unit 118 may be a defibrillator unit, a cardioverter/defibrillator unit, or a multi-modal cardiac therapy unit similar to the cardiac stimulator disclosed by Haluska et al. in U.S. Pat. No. 4,830,006, or any other type of anti-arrhythmic therapy unit known in the art.

The anti-arrhythmic electrodes 120 are adapted to be suitable for the delivery of the specific types of anti-arrhythmic therapy signals which the anti-tachyarrhythmic unit 118 is capable of applying to the heart. For example, the anti-arrhythmic electrodes 120 may comprise one or more electrodes adapted for delivering signals to the heart such as, but not limited to, high energy defibrillating shock signals, non-defibrillating cardioversion signals, ATP signals, and the like. The microprocessor unit 106 is suitably connected to a data bus 122. The data bus 122 is connected to one or more memory units 124, one or more timing units 126 and to a telemetry unit 128. The microprocessor unit 106 may store and retrieve data on the memory units 124. The memory units 124 may include memory units including embedded read only data such as programs for operating the microprocessor unit 106 to control and operate the device 100. The memory units 124 may also include memory units having read and write capabilities for data storage and retrieval (such as, but not limited to, RAM memory units) for storing, inter alia, patient data, computational results, and programming instructions which are telemetrically or non-telemetrically communicated to the CCM device 100. The timing units 126 provide timing or clocking signals to the microprocessor unit 106 over the data bus 122. The microprocessor unit 106 communicates with the memory units 124, the timing unit(s) 126 and the telemetry device 128 over the data bus 122. The telemetry device 128 is optional and enables wireless data transmission to and from a telemetry transceiver unit (not shown) disposed outside the patient (not shown).

In operation, the delivery of CCM signals to the heart by the CCM unit 108 is controlled based on the output of the detecting units 112 to the microprocessor unit 106, as disclosed in detail in the above referenced co-pending U.S. patent applications Ser. Nos. 09/276,460, 09/328,068 and 09/338,649 to Mika et al., and in the corresponding PCT applications.

In accordance with one preferred embodiment of the present invention, the CCM unit 108 provides control signals to one or more of the sensing units 112 and/or to one or more of the detecting units 116 for inducing refractory periods in the sensing unit(s) 112 or in the detecting units 116 or in the sensing unit(s) 112 and the detecting units 116 as disclosed in detail hereinabove, for preventing interference of CCM induced electrical artifact signals with the sensing or the detecting or both sensing and detecting of depolarization events as disclosed hereinabove. The control signals may be (optionally) provided from the CCM unit 108 to the sensing unit 112 as represented by the dashed arrow 130. The control signals may also be (optionally) provided from the CCM unit 108 to the detecting unit(s) 116 as represented by the dashed arrow 132. The control signals may also be simultaneously provided to the sensing unit(s) 112 and to the detecting unit(s) 116 as disclosed hereinabove.

Alternatively, in accordance with another preferred embodiment of the present invention, the control signals may be provided from the microprocessor unit 106 to the sensing unit(s) 112 or to the detecting unit(s) 116 or to both of the sensing unit(s) 112 and the detecting unit(s) 116 as disclosed in detail hereinabove. The sensing unit(s) 112 or the detecting unit(s) 116 or both the sensing unit(s) 112 and the detecting unit(s) 116 may be switched by the control signals into a refractory state as disclosed hereinabove.

Furthermore, in accordance with yet another preferred embodiment of the present invention, the microprocessor unit 106 may use the data of the timing of the delivery of CCM signals to the heart for performing a correcting or compensating method or computation in order to prevent errors at the classification level as disclosed in detail hereinabove.

It is noted that, the sensing units 112 may include a plurality of sensing units operative for providing sensing at different sites of the heart, such as but not limited to, the right atrium, the right ventricle, the left ventricle of the heart and other different cardiac sites in order to provide the various sensing configurations required for the operation of any of the specific type or configuration of the anti-tachyarrhythmic unit 118 which is implemented in the device 100, any of the specific configurations or modes of anti-bradycardia pacing therapy which may be implemented on the pacing unit 102, and any of the specific sensing configurations required for operating the CCM unit 108, including but not limited to, the sensing methods and configurations disclosed in the PCT publications to Ben Haim et al. and in the co-pending U.S. patent applications Ser. Nos. 09/276,460, 09/328,068 and 09/338,649 to Mika et al. referenced hereinabove, and in the corresponding PCT applications.

In order to prevent or at least to reduce the probability of the misclassification and the resulting delay or failure of the proper application of anti-arrhythmic therapy, the device 100 is adapted to use the threshold based method to disable the delivery of CCM signals to the heart when the detected heart rate exceeds a certain threshold as is disclosed in detail for the device 51 of FIG. 3.

Thus, in accordance with a preferred embodiment of the present invention, the device 100 continuously determines the heart rate and classifies the heart rate, in accordance with any sensing, detecting, and anti-arrhythmic heart rate classification methods or algorithms known in the art. Simultaneously, the CCM unit 108 and the microprocessor unit 106 operate to detect the need for CCM therapy and to control the delivery of CCM signals to the heart, in accordance with any of the methods of CCM signal delivery known in the art or disclosed in any of the above referenced published or co-pending patent applications disclosed hereinabove. If the heart rate exceeds a certain threshold level, this heart rate is classified as a suspected tachy-arrhythmia and the microprocessor 106 disables the delivery of CCM signals to the heart within the CCM signal free period, disclosed hereinabove.

Typically, the heart rate is determined by determining the R-R interval as is known in the art, but other methods may also be used.

The threshold level value for determining the suspected tachy-arrhythmia is preferably individually adapted to each patient and then set by programming it into the memory unit(s) 124 by communicating it telemetrically or non-telemetrically to the device 100 as is known in the art. This individual determination and setting of the value of the heart rate threshold level for suspected tachy-arrhythmia has the advantage of enabling to fine-tune the operation of the device 100 such as to find an appropriate balance between minimizing undesired masking, delayed detection, or non-detection of therapy requiring tachy-arrhythmic episodes due to use of the above disclosed refractory period and maximizing the upper heart rate level at which CCM therapy may still be delivered to the heart.

The precise value of the acceptable threshold level may be influenced, inter alia, by the type of cardiac disorder of the patient, the presence or absence of cardio-therapeutic drugs used by the patient, and data collected in the same patient under normal cardiac conditions, SVT conditions, VT conditions and possibly VF conditions. The setting of the threshold value may have to be performed by a physician or cardio-physiologist based on study of such patient conditions and on the degree of desired CCM modification for that patient.

Typically, an exemplary non-limiting value for the heart rate threshold level is 150 heart beats per minute. However, other larger or smaller threshold level values may also be used, according to the individual patient cardiac conditions.

The disabling of the delivery of CCM signals is performed by the microprocessor unit 106 by sending appropriate control signal or signals to the CCM unit 108. The device 100 then continues to determine the heart rate within this CCM signal free period in the absence of CCM signal delivery. The microprocessor 106 of the device 100 analyzes and classifies the heart rate in accordance with the classification criteria based on the detection signal data which are sent from one or more of the detecting units 116 to the microprocessor unit 106 during the CCM signal free period. The microprocessor 106 of the device 100 then determines whether any type of anti-arrhythmia therapy is to be delivered to the heart based on the classification of the heart rate obtained in the CCM free period.

If the classification of the heart rate resulting from the processing of the detection data obtained in the CCM free period indicates the need to deliver any type of anti-arrhythmic therapy, the microprocessor 106 continues the disabling of CCM signal delivery and initiates the delivery of the required anti-arrhythmic therapy by sending appropriate control signals to the anti-tachyarrhythmic unit 118, and continues to deliver any indicated anti-arrhythmic therapy and to determine and classify the heart rate as is known in the art until the anti-arrhythmic therapy is terminated. If the anti-arrhythmic therapy is terminated by the microprocessor 106, the microprocessor 106 enables the delivery of CCM signals to the heart by sending a suitable enabling control signal to the CCM unit 108.

If the classification of the heart rate obtained in the CCM free period does not indicate a need to deliver any type of anti-tachyarrhythmic therapy, the microprocessor 106 enables the delivery of CCM signals to the heart by sending a suitable enabling control signal to the CCM unit 108.

Similar to the method disclosed for the device 51 of FIG. 3, the anti-tachyarrhythmia detection and classification program, sub-routine, or algorithm operative on the microprocessor unit 106 takes priority over the CCM delivery control program, sub-routine, or algorithm which is also operative on the microprocessor unit 106, enabling it to override, interrupt or disable the CCM signal delivery even under conditions in which the delivery of CCM signals is called for by the CCM delivery control program to modify cardiac contractility and or cardiac output.

Preferably, but not necessarily, the detection of bradycardia and the delivery of anti-bradycardia pacing therapy is performed by pacing programs, subroutines or algorithms which are operative on the microprocessor 106 as is known in the art and disclosed hereinabove.

It is noted that, if the sensing unit(s) 112 include a plurality of sensing units operative for providing sensing of signals at different sites of the heart, the sensing units 112 may be, but need not necessarily be, identical units and may differ from each other to be adapted for sensing specific signals.

Similarly if the detecting units 116 include a plurality of detecting units operative for providing event detecting for signals sensed at different sites of the heart, the detecting units 116 may be, but need not necessarily be, identical units and may differ from each other to be adapted for detection of specific sensed and amplified signals.

It is noted that the CCM devices 30, 51 and 100 of FIGS. 2, 3 and 4, respectively, may be adapted for acute implantation in a patient for short term patient monitoring and therapy treatment such as for temporary use in intensive care hospitalized patient's. Alternatively, the CCM devices 30, 51 and 100 of FIGS. 2, 3 and 4, respectively, may be adapted for used as implantable devices for chronic implantation.

It will be appreciated that the preferred embodiments disclosed hereinabove and illustrated in the drawings are given by way of example only and that many variations and modifications of the present invention may be made which are within the scope and spirit of the present invention.

The invention claimed is:

1. A cardiac contractility modulating device comprising:
an anti-arrhythmic therapy unit for detecting a cardiac arrhythmia in a heart of a patient based on processing electrical signals related to cardiac activity of said heart and for delivering anti-arrhythmic therapy to said heart in response to detecting of said cardiac arrhythmia;
a cardiac contractility modulating unit configured for delivering cardiac contractility modulating signals to said heart for modulating the contractility of at least a portion of said heart, said cardiac contractility modulating unit is operatively connected to said anti-arrhythmic unit for providing said anti-arrhythmic therapy unit with first control signals associated with the delivery of said cardiac contractility modulating signals to said heart to prevent interference of said cardiac contractility modulating signals with said detecting of said cardiac arrhythmia by said anti-arrhythmic device;
a telemetry unit in communication with at least one of said anti-arrhythmic therapy unit and said cardiac contractility modulating unit, said telemetry unit is configured for telemetrically communicating with a telemetry transceiver; and
at least one power source for energizing said anti-arrhythmic therapy unit, said cardiac contractility modulating unit and said telemetry unit.

2. Apparatus according to claim 1, wherein said telemetry unit controls one of said anti-arrhythmic therapy unit and said cardiac contractility modulating unit.

3. Apparatus according to claim 1, wherein said telemetry unit controls both said anti-arrhythmic therapy unit and said cardiac contractility modulating unit.

4. Apparatus according to claim 1, wherein said anti-arrhythmic unit comprises a receiver for receiving control signals from said cardiac contractility modulating unit.

5. Apparatus according to claim 1, wherein said first control signals are directly delivered from said cardiac contractility modulating unit to said anti-arrhythmic therapy unit.

6. A cardiac contractility modulating device comprising:
an anti-arrhythmic therapy unit for detecting a cardiac arrhythmia in a heart of a patient based on processing electrical signals related to cardiac activity of said heart and for delivering anti-arrhythmic therapy to said heart in response to detecting of said cardiac arrhythmia;
a cardiac contractility modulating unit configured for delivering cardiac contractility modulating signals to said heart for modulating the contractility of at least a portion of said heart, said cardiac contractility modulating unit is operatively connected to said anti-arrhythmic unit for providing said anti-arrhythmic therapy unit with control signals associated with the delivery of said cardiac contractility modulating signals to said heart to prevent interference of said cardiac contractility modulating signals with said detecting of said cardiac arrhythmia by said anti-arrhythmic device;

and at least one power source for energizing said anti-arrhythmic therapy unit, said cardiac contractility modulating unit and a telemetry unit, wherein said anti-arrhythmic therapy unit comprises a sensing unit for sensing said electrical signals and a detecting unit for detecting cardiac activity related events in said electrical signals, said sensing unit is configured for stopping the sensing of said electrical signals within a refractory time period in response to receiving one of said first control signals, and said detecting unit is configured for stopping said detecting of said cardiac activity related events within said refractory time period in response to receiving one of said control signals.

7. The device according to claim 6 wherein said refractory period begins before the application of a cardiac contractility modulating signal to the heart and ends after the application of said cardiac contractility modulating signal to the heart.

8. The device according to claim 6 wherein said cardiac contractility modulating unit is configured for varying the parameters of said cardiac contractility modulating signals in response to different detected cardiac conditions and to vary the parameters of said refractory period based on the parameters of the cardiac contractility modulating signal on a beat by beat basis.

9. A cardiac contractility modulating device comprising:
arrhythmia detection means configured for detecting a cardiac arrhythmia in a heart of a patient based on processing electrical signals related to cardiac activity of said heart;
anti-arrhythmic therapy means for applying anti-arrhythmic therapy to said heart in response to detecting of said cardiac arrhythmia; and
cardiac contractility modulating means configured for delivering cardiac contractility modulating signals to said heart to modulate the contractility of at least a portion of said heart, said cardiac contractility modulating means being operatively connected to said arrhythmia detection means for providing said arrhythmia detection means with control signals associated with the delivery of said cardiac contractility modulating signals to said heart to prevent interference of said cardiac contractility modulating signals with the detecting of said cardiac arrhythmia by said arrhythmia detection means.

10. A cardiac contractility modulating device comprising:
an anti-arrhythmic therapy unit for detecting a cardiac arrhythmia in a heart of a patient based on processing electrical signals related to cardiac activity of said heart and for delivering anti-arrhythmic therapy to said heart in response to detecting of said cardiac arrhythmia, said anti-arrhythmic therapy unit is configured for disabling for a preset time period the delivery of cardiac contractility modulating signals to said heart when the heart rate of said patient exceeds a threshold value;

a cardiac contractility modulating unit configured for delivering cardiac contractility modulating signals to said heart for modulating the contractility of at least a portion of said heart, said cardiac contractility modulating unit is operatively connected to said anti-arrhythmic unit for providing said anti-arrhythmic therapy unit with first control signals associated with the delivery of said cardiac contractility modulating signals to said heart to prevent interference of said cardiac contractility modulating signals with said detecting of said cardiac arrhythmia by said anti-arrhythmic device; and at least one power source for energizing said anti-arrhythmic therapy unit, said cardiac contractility modulating unit, and a telemetry unit.

11. A method for applying anti-arrhythmic therapy to a heart of a patient, the method comprising the steps of:
providing a cardiac contractility modulating device configured for applying cardiac contractility modulating signals to the heart of said patient;
sensing electrical signals associated with cardiac activity of said patient;
detecting in said electrical signals cardiac events associated with said cardiac activity for determining the heart rate of said patient;
disabling the delivery of cardiac contractility modulating signals to said heart when heart rate of said heart exceeds a threshold value to provide a cardiac contractility modulating signal free time period;
processing the data obtained during said cardiac contractility modulating signal free time period to detect a cardiac arrhythmia; and
delivering anti-arrhythmic therapy to the heart of said patient if an arrhythmia is detected.

12. The method according to claim 11 wherein said determining of said heart rate is based on determining the R-R intervals within said cardiac contractility modulating signal free time period.

13. The method according to claim 11 wherein said threshold value is determined from empirical data recorded in said patient.

14. The method according to claim 11 further including enabling the delivery of cardiac contractility modulating signals to said heart after terminating the delivering of said anti-arrhythmic therapy to said heart.

15. The method according to claim 11 wherein said processing comprises classifying the determined heart rate according to a classification method adapted to determine the suspected occurrence of different types of arrhythmias based on the determined heart rate, and controlling the delivery of a selected type of anti-arrhythmic therapy to said heart in response to detection of a suspected arrhythmia type.

16. The method according to claim 11 wherein said anti-arrhythmic therapy is selected from defibrillating shock therapy, cardioverting shock therapy, anti-tachycardia pacing therapy, anti-bradycardia pacing therapy, variable energy shock therapy, and combinations thereof.

17. The method according to claim 11 further including pacing at least one chamber of said heart of said patient.

18. The method according to claim 11 wherein said sensing is performed at one or more sites of said heart.

* * * * *